US008916347B2

(12) United States Patent
Goel et al.

(10) Patent No.: US 8,916,347 B2
(45) Date of Patent: Dec. 23, 2014

(54) INTEGRATED MICROFLUIDIC AND SOLID STATE PYROSEQUENCING SYSTEMS

(75) Inventors: Sanket Goel, Singapore (SG); Min Gong, Singapore (SG); Abdur Rub Abdur Rahman, Singapore (SG); Shihui Foo, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/579,666

(22) PCT Filed: Feb. 21, 2011

(86) PCT No.: PCT/SG2011/000070
§ 371 (c)(1),
(2), (4) Date: Aug. 17, 2012

(87) PCT Pub. No.: WO2011/102808
PCT Pub. Date: Aug. 25, 2011

(65) Prior Publication Data
US 2013/0045876 A1     Feb. 21, 2013

Related U.S. Application Data

(60) Provisional application No. 61/306,313, filed on Feb. 19, 2010.

(51) Int. Cl.
*C12Q 1/68* (2006.01)
*C12Q 1/66* (2006.01)
*C12P 19/34* (2006.01)
*B01L 7/00* (2006.01)
*B01L 3/00* (2006.01)

(52) U.S. Cl.
CPC ............... *C12Q 1/6869* (2013.01); *B01L 7/52* (2013.01); *B01L 2200/0642* (2013.01); *B01L 2400/0487* (2013.01); *B01L 2400/0415* (2013.01); *B01L 3/502761* (2013.01)
USPC .............................. 435/6.1; 435/8; 435/91.1

(58) Field of Classification Search
None
See application file for complete search history.

(56) References Cited

U.S. PATENT DOCUMENTS

| | | | |
|---|---|---|---|
| 6,258,568 B1 * | 7/2001 | Nyren | 435/91.1 |
| 6,291,164 B1 | 9/2001 | Blakesley | |
| 7,648,824 B2 | 1/2010 | Nyren et al. | |
| 2003/0232021 A1 | 12/2003 | Schechter | |
| 2004/0242532 A1 | 12/2004 | Meyer | |
| 2007/0166729 A1 | 7/2007 | Kambara et al. | |
| 2010/0021915 A1 | 1/2010 | Khan | |

FOREIGN PATENT DOCUMENTS

WO    WO-2011/102808 A1    8/2011

OTHER PUBLICATIONS

Alderborn et al., "Determination of Single-Nucleotide Polymorphisms by Real-time Pyrophosphate DNA Sequencing," Genome Res. 2000, 10:1249-1258.*
Lee et al., "Enhancing ATP-based bacteria and biofilm detection by enzymatic pyrophosphate regeneration," Anal. Biochem. 2010, 399:168-173, published online Jan. 4, 2010.*
International Search Report and Written Opinion for PCT/SG2011/000070 mailed May 2, 2011.
International Preliminary Report on Patentability for PCT/SG2011/000070 mailed Aug. 30, 2012.
Eisaki et al., Pyruvate phosphate dikinase from a thermophilic actinomyces Microbispora rosea subsp. aerata: purification, characterization and molecular cloning of the gene. Biochim Biophys Acta. May 18, 1999;1431(2):363-73.
Zhou et al., Enzyme system for improving the detection limit in pyrosequencing. Analytical Chem. 2006;78(13):4482-9. 9 (The year of publication is sufficiently earlier than the effective U.S. filing and any foreign priority date so that the particular month of publication is not in issue. See MPEP 609.04(a)).
Agah et al., Multi-enzyme model for pyrosequencing. Nucleic Acids Research. 2004;32(21):e166.
Arakawa et al., Development of bioluminescent pyrophosphate assay using pyruvate phosphate dikinase and its application to single-nucleotide polymorphism analysis. Anal Biochem. Aug. 1, 2008;379(1):86-90. Epub Apr. 25, 2008.
Ballicora et al., ADP-Glucose Pyrophosphorylase: A Regulatory Enzyme for Plant Starch Synthesis. Photosynth Res. 2004;79(1):1-24.
Beckers et al., Rapid diagnosis of bacteraemia by measuring bacterial adenosine triphosphate in blood culture bottles using bioluminescence. Med. Microbiol. Immunol. 1983;172:117-22.
Ching, A rapid and sensitive assay of ADP glucose pyrophosphorylase using luciferase. Anal Biochem. Mar. 1, 1981;111(2):327-30.
Diggle et al., Pyrosequencing: sequence typing at the speed of light. Mol Biotechnol. Oct. 2004;28(2):129-37.
Fusari et al., A colorimetric method for the assay of ADP-glucose pyrophosphorylase. Anal Biochem. May 1, 2006;352(1):145-7. Epub Feb. 2, 2006.
Gharizadeh et al., Methodological improvements of pyrosequencing technology. Journal of Biotechnology. 2006;124:504-11.
Gong et al., "Alternate Enzyme System for Pyrosequencing to Increase the Detection Limit", Abstract A00304, 14th Human Genome Meeting 2010, May 2010 http://www.hgm2010.org/viewabsdetail-word.php/?id=467&pn=P152-T.
Gordon, Extracellular ATP: effects, sources and fate. Biochem J. Jan. 15, 1986;233(2):309-19.
Iglesias et al. Expression of the Potato Tuber ADP-glucose Pyrophosphorylase in *Escherichia coli*. Journal of Biological Chemistry. 1993;268(2):1081-6.
Kedes et al., Genomics prize—the X Prize Foundation. Interview by Vicki Glaser. Rejuvenation Res. Jan. 2007;10(2):237-42.

(Continued)

*Primary Examiner* — Samuel Woolwine
*Assistant Examiner* — Kaijiang Zhang
(74) *Attorney, Agent, or Firm* — Wolf, Greenfield & Sacks, P.C.

(57) ABSTRACT

The invention provides for sequencing a nucleic acid molecule based on the detection of base incorporation by the release of pyrophosphate (PPi) using a new enzyme system comprising adenosine diphosphate (ADP)-glucose pyrophosphorylase (AGPase) and its substrate ADP-glucose.

10 Claims, 34 Drawing Sheets

(56) References Cited

OTHER PUBLICATIONS

Magnan, Detection of visible photons in CCD and CMOS: A comparative view. Nuclear Instruments and Methods in Physics Research A. 2003;504:199-212.

Mardis, Next-Generation DNA Sequencing Methods. Annual Review of Genomics and Human Genetics. 2008;9: 387-402.

Nakamura et al., Cell-surface-localized ATP detection with immobilized firefly luciferase. Anal Biochem. May 1, 2008;352(1):61-7. Epub Mar. 9, 2006.

Priess, Biosynthesis of Starch and its Regulation. Biochemistry of Plants, Academic Press, US. Jan. 1998;14:181-254.

Ronaghi et al., A sequencing method based on real-time pyrophosphate. Science. Jul. 17, 1998;281(5375):363-365.

Ronaghi et al., Real-time DNA sequencing using detection of pyrophosphate release. Anal Biochem. Nov. 1, 1996;242(1):84-9.

Satoh et al., ATP amplification for ultrasensitive bioluminescence assay: detection of a single bacterial cell. Biosci Biotechnol Biochem. Jun. 2004;68(6):1216-20.

Schneider et al., Continuous detection of extracellular ATP on living cells by using atomic force microscopy. PNAS. 1999;96:12180-5.

Shendure et al. Next-generation DNA sequencing. Nat Biotechnol. Oct. 2008;26(10):1135-45.

Whitehead et al., The detection of food soils and cells on stainless steel using industrial methods: UV illumination and ATP bioluminescence. Int J Food Microbiol. Sep. 30, 2008;127(1-2):121-8. Epub Jun. 27, 2007.

* cited by examiner

SEQUENCE LISTING

```
<160> NUMBER OF SEQ ID NOS: 19

<210> SEQ ID NO 1
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 1
cgtaccggtt aa                                                          12

<210> SEQ ID NO 2
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 2
gtattgacgc cgggc                                                       15

<210> SEQ ID NO 3
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 3
ggccaactta cttctg                                                      16

<210> SEQ ID NO 4
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 4
tactcctacc cgcacccctg cccccttccc cccgc                                 35

<210> SEQ ID NO 5
<211> LENGTH: 21
<212> TYPE: DNA
<213> ORGANISM: Artificial Sequence
<220> FEATURE:
<223> OTHER INFORMATION: Synthetic Oligonucleotide
```

<400> SEQUENCE: 5
gttatctttt tttttctcg t                                         21

<210> SEQ ID NO 6
<211> LENGTH: 74
<212> TYPE: DNA
<213> ORGANISM: Artificial Sequence
<220> FEATURE:
<223> OTHER INFORMATION: Synthetic Oligonucleotide

<400> SEQUENCE: 6
tggtttattg ctgataaatc tggagccggt gagcgtgggt ctcgcggtat cattgcagca    60
ctggggccag atgg                                                      74

<210> SEQ ID NO 7
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 7
cgtagactcc ttggaagcat aaggccttga t                              31

<210> SEQ ID NO 8
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 8
ggactataaa gataccaggc gtt                                       23

<210> SEQ ID NO 9
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 9
taaccggtac gaacgcctgg tatctttata gtccatc                        37

<210> SEQ ID NO 10
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 10
atcaaggcct tatgcttcca aggagtctac gaacgcctgg tatctttata gtccatc     57

<210> SEQ ID NO 11
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 11
ctgcgggggg aagggggcag gggtgcgggt aggagtaaac gcctggtatc tttatagtcc    60
a                                                                    61

<210> SEQ ID NO 12
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 12
acgagaaaaa aaaaagataa caacgcctgg tatctttata gtcca            45

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 13
ataactacga tacgggaggg                                         20

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 14
gctatgtggc gcggtattat                                         20

<210> SEQ ID NO 15
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 15
cttccggctg gc                                                 12

<210> SEQ ID NO 16
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 16
gcgcggtatt atccc                                              15

<210> SEQ ID NO 17
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 17
gataacactg c                                                  11

<210> SEQ ID NO 18
<211> LENGTH: 37
<212> TYPE: DNA
<213> ORGANISM: Artificial Sequence
<220> FEATURE:

```
<223> OTHER INFORMATION: Synthetic Oligonucleotide

<400> SEQUENCE: 18
aacgacccgg ccgaacgcct ggtatcttta tagtcca                              37

<210> SEQ ID NO 19
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 19
aacgacccgg ccaaacgcct ggtatcttta tagtcca                              37
```

INTEGRATED MICROFLUIDIC AND SOLID STATE PYROSEQUENCING SYSTEMS

This application is a U.S. national stage application based on International Application No. PCT/SG2011/000070, filed Feb. 21, 2011, which claims the benefit of priority of U.S. provisional application No. 61/306,313, filed Feb. 19, 2010, the contents of each of which is incorporated herein by reference in its entirety.

FIELD OF THE INVENTION

The invention relates generally to analyzing nucleic acid molecules. More particularly, the invention relates to systems for sequencing nucleic acid molecules based on the detection of base incorporation by the release of pyrophosphate (PPi).

BACKGROUND OF THE INVENTION

DNA sequencing is considered to be among the top priorities in the biosciences field today. Advances in the sequencing of entire genomes, their annotation and variations have been the critical enabling factors for biological research. Following the completion of the human genome project, there has been continuing work in the detection of genetic variations in a large number of samples representing a broad range of biological material, which provides an insight into genetic mechanisms of different diseases.

Enzymatic chain-termination or the Sanger method, and the chemical cleavage technique of Maxam and Gilbert are examples of two methods for DNA sequencing, which rely on gel electrophoresis to resolve DNA fragments produced from a larger DNA segment.

Pyrosequencing is another method for sequencing DNA. This method does not rely on electrophoretic separation. Pyrosequencing refers to a bioluminometric DNA sequencing technique that measures the release of pyrophosphate during DNA synthesis. The existing pyrosequencing methods are typically real-time bioluminescence-based sequencing-by-synthesis methods catalyzed by four kinetically well-balanced enzymes. Such enzymes may be DNA polymerase, ATP sulfurylase, firefly luciferase and apyrase. A DNA sample, at picomole level, is usually used in the existing pyrosequencing methods based on a luciferase assay coupled with an APS-ATP surfurylase reaction for producing ATP from PPi. In the presence of DNA polymerase, correct nucleotide incorporation into the DNA sample leads to generation of pyrophosphate (PPi) in a quantity equimolar to the number of incorporated nucleotides. The released PPi then triggers the ATP sulfurylase reaction resulting in a quantitative conversion of PPi to ATP. ATP is subsequently consumed by luciferase for producing bioluminescence, which is proportional to the amount of DNA and the number of incorporated nucleotides. In pyrosequencing, the unincorporated nucleotides and the generated ATP can be degraded by apyrase allowing iterative addition of the next nucleotide dispensation to the solution. An existing pyrosequencing method based on ATP-sulfurylase may be represented by the following reaction cascade:

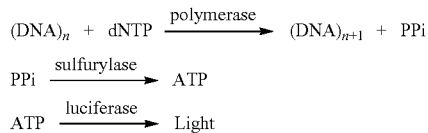

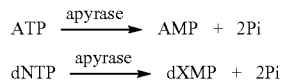

Even though the existing pyrosequencing methods are based on a sensitive bioluminometric assay, they still require DNA templates or samples at a picomole level, which may be challenging in some applications. Although the luminescence intensity could be increased by increasing the amount of luciferase, a large background signal due to a side reaction of APS with luciferase introduces limitations to the existing assays.

Several sequencing platforms are currently in use, however their cost can be prohibitive. Despite strong research initiatives having been launched in the area of sequencing, it appears that, at present, no technology can address the issues of cost, time and accuracy simultaneously, and in particular, to be able to sequence a human genome under about one thousand dollars USD and within a day. Therefore there remains a need for an improvement in the methods and systems for analyzing nucleic acid molecules.

SUMMARY OF THE INVENTION

In accordance with one aspect of the invention, there is provided a use of adenosine diphosphate (ADP)-glucose pyrophosphorylase (AGPase) for sequencing a nucleic acid molecule. In various aspects, the use further comprises ADP-glucose, which is a substrate of the adenosine diphosphate (ADP)-glucose pyrophosphorylase.

In various further aspects of the use, the sequencing comprises converting PPi to ATP in DNA sequencing based on a detection of base incorporation by a release of PPi, which may be pyrosequencing. In various aspects, the use provides for obtaining a low background signal and a high sample signal in the presence of a large amount of luciferease, which may range from about 0.3 μg to about 3 μg in concentration. In various aspects, the use provides for obtaining a distinguishable signal for a homopolymeric DNA region, for developing on a large-scale pooled DNA sample a high throughput allele frequency, sequencing monopolymeric or homopolymeric regions which may comprise up to 10 consecutive nucleotides, sequencing a DNA having more than about 70 bases or having about 5% allele frequencies. In various other aspects, the use can yield a read-length of about 400 to about 1000 base pairs.

In yet other aspects, the use provides for sequencing a DNA sample having a concentration of about 0.025 pmol or less to about 2 pmol, from about 2 pmol to about 15 pmol, or from about 0.025 pmol or less to about 15 pmol of a nucleic acid such as DNA. In various aspects, the nucleic acid (e.g. DNA) may be unamplified, amplified or both. The amplified nucleic acid may comprise a nucleic acid obtained from PCR, an insert in a vector, an insert in a plasmid, or a combination thereof. In other aspects, the use further comprises using luciferase, a nucleotide degrading enzyme such as apyrase or a combination thereof.

In various aspects of the use, the DNA sequencing can be step-wise sequencing or continuous sequencing, which may be monitored in real time. In further aspects of the use, the sequencing comprises sequencing a single-stranded DNA, which may be in solution or immobilized on a solid support. In various aspects of the use, the solid support may be chemically modified to comprise a functional group, a moiety or a combination thereof, and may comprise a particle, a fiber, a capillary, an array or a combination thereof. In further aspects, the solid support may be washed following a reaction, an addition of a reagent, or a combination thereof.

In further aspects, there is provided an apparatus for simultaneous analysis of multiple nucleic acid molecules, which may be, for example, pyrosequencing.

The pyrosequencing may be de novo genome sequencing, ultra-high throughput pyrosequencing, paired-end ditagging, or real-time pyrosequencing.

In various aspects, the apparatus comprises a reaction platform comprising a plurality of wells, each of the plurality of wells entrapping a sample solid support having an immobilized sample nucleic acid molecule. In yet further aspects, the reaction platform is silicon-based, polymer-based or a combination thereof, and may be chemically modified. The sample solid support may comprise a bead, a particle, a fiber, or a capillary. The apparatus further comprises a reagent source in fluid communication with each of the plurality of wells for flowing a reagent to each of the plurality of wells and for transporting a product away from each of the plurality of wells while the sample solid support remains entrapped in the respective well, and an imaging sensor mounted on the reaction platform for acquisition of chemiluminescence intensity from each of the plurality of wells. In various aspects, the reagent source may comprise a nucleotide, a buffer, an enzyme or a combination thereof. The imagining sensor may be a CMOS image sensor or a CCD image sensor.

In various other aspects, the apparatus may further comprise a thermal system for modulating a temperature of the reagent source, the reaction platform, the imaging sensor, or a combination thereof. In various aspects, the temperature of the reagent is about 5° C., and the temperature of the reaction platform, the imaging sensor, or a combination thereof is about 0° C.

In various aspects of the apparatus, the plurality of reaction wells may comprise an array of microwells, which may be photolithographically fabricated, wherein each of the microwells may have a depth of about 45 μm. In various aspects of the apparatus, the reaction platform may be a fiberoptic plate.

In various aspects the apparatus may further comprise a reagent solid support comprising the reagent, the reagent solid support being disposed in each of the plurality of reaction wells. The reagent may comprise polymerase, adenosine diphosphate (ADP)-glucose pyrophosphorylase, PPDK, luciferase, apyrase, ADP-glucose, or a combination thereof. In yet further aspects, the apparatus may comprise a packing support disposed in each of the plurality of wells for providing packing within each of the wells, reducing delamination, or loss of the sample solid support, the reagent solid support or both.

In further aspects of the apparatus, the acquisition of chemiluminescence intensity from each of the plurality of reaction wells can be synchronized with a reagent flow from the reagent source to the reaction platform.

In various aspects of the apparatus, the nucleic acid sample comprises unamplified DNA, amplified DNA, or a combination thereof. In various aspects, the nucleic acid sample comprises about 0.025 pmol DNA or less. In various aspects of the apparatus, the sequencing comprises sequencing a few genomes per day, or sequencing ranging from a few kilobases to a few hundred megabases.

In various aspects of the apparatus, the reagent source, the reaction platform and the imaging sensor form an integrated system, an automated system, or both an integrated and an automated system for pyrosequencing the nucleic acid sample. The apparatus may also be re-usable.

In yet further aspects, there is provided a method for sequencing a target nucleic acid molecule. The method comprises contacting the target nucleic acid molecule with a pyrophosphate sequencing reagent. The pyrophosphate sequencing reagent comprises a nucleotide triphosphate, a polymerase, a pyrophosphate to ATP converting enzyme comprising adenosine diphosphate (ADP)-glucose pyrophosphorylase, a substrate ADP-glucose or a combination thereof, and an ATP detecting enzyme. The method further comprises detecting a resulting optical signal wherein the optical signal is indicative of a reaction of the pyrophosphate sequencing reagent with the target nucleic acid molecule, thereby sequencing the nucleic acid molecule.

In various embodiments, the pyrophosphate sequencing reagent further comprises a nucleotide degrading enzyme such as apyrase. In various embodiments, the ATP detecting enzyme is luciferase. In yet further embodiments, the target nucleic acid molecule comprises a concentration of DNA of about 0.025 pmol or less to about 2 pmol, from about 2 pmol to about 15 pmol, or from about 0.025 pmol or less to about 15 pmol. The target nucleic acid molecule may be immobilized on a solid support such a bead.

In yet another embodiment, there is provided a kit for identifying a base at a target position in a sample DNA sequence. The kit comprises a polymerase, a nucleotide triphosphate, a pyrophosphate to ATP converting enzyme comprising adenosine diphosphate (ADP)-glucose pyrophosphorylase (AGPase) and a substrate ADP-glucose, and an ATP detecting enzyme. The kit may further comprise a nucleotide degrading enzyme such as apyrase. The kit may be used in analyzing a sample DNA sequence comprising a concentration of DNA of about 0.025 pmol or less to about 2 pmol, from about 2 pmol to about 15 pmol, or from about 0.025 pmol or less to about 15 pmol.

BRIEF DESCRIPTION OF THE DRAWINGS

In accompanying drawings which illustrate embodiments of the invention,

FIG. 2 illustrates optimization of the AGPase-based pyrosequencing system according to an embodiment of the invention. Pyrosequencing data was obtained from 1pmol DNA.

FIG. 5 shows AGPase-based pyroseqeunicng for templates containing various homopolymeric regions according to an embodiment of the invention. Pyrosequencing data was obtained from 1 pmol DNA.

FIG. 7 shows allelic frequency determination obtained on mixtures of two different synthesized oligos. Proportions were: FIG. 7A, 100% C; FIG. 7B, 95% C: 5% A; FIG. 7C, 50% C: 50% A; FIG. 7D, 5% C: 95% A; FIG. 7E, 100% A. Pyrosequencing data was obtained from 1 pmol DNA;

FIG. 9 shows a comparison among an ATP sulfurylase-based pyrosequencing system, an AGPase-based pyrosequencing system according to an embodiment of the present invention, and a PPDK-based pyrosequencing system. 0.1 pmol of DNA was sequenced using: FIG. 9D, 0.025 pmol of DNA sequenced using AGPase-based system. The oligo sequence order: CGTAGACTCCTTGGAAGCATAAGGCCTTGAT (SEQ ID NO:7). dNTP dispensing order was A>T>G>C;

DETAILED DESCRIPTION

Figure 1:
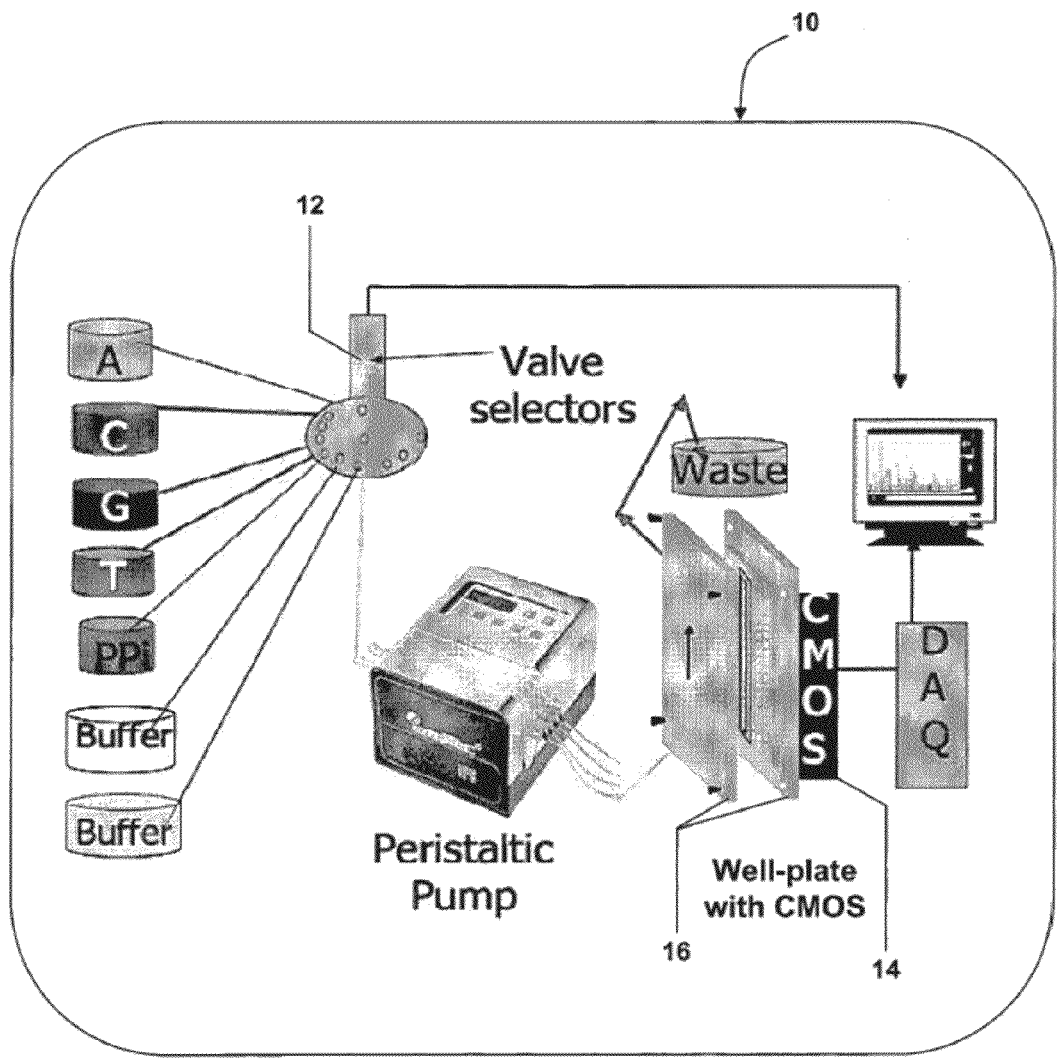
FIG. 1 illustrates a schematic diagram of the sequencing system according to an embodiment of the present invention.

Reference will now be made in detail to implementations and embodiments of various aspects and variations to the invention, examples of which are illustrated in the accompanying drawings.

In one aspect, the present invention relates to a new enzyme system for use in sequencing a nucleic acid molecule based on a conversion of PPi to ATP. In other aspects, the present invention relates to a method, a kit and an apparatus of using the new enzyme system. In various aspects, the new enzyme system may be used in any analysis relating to a nucleic acid molecule or sequencing of a nucleic acid molecule which comprises a conversion of PPi to ATP, with pyrosequencing being an example of such an analysis. In various embodiments, the new enzyme system comprises adenosine diphosphate (ADP)-glucose pyrophosphorylase (AGPase-based system), its substrate ADP-glucose, or a combination thereof to convert PPi to ATP.

Traditionally, ADP-glucose pyrophosphorylase has been used to control starch synthesis by catalyzing the conversion of glucose-1-phosphate to ADP-glucose, where ATP functions as a substrate and pyrophosphate (PPi) is produced. The new enzyme system according to various embodiments of the present invention leverages upon the reverse enzymatic reaction of AGPase (where $V_{max}$ is double that for forward reaction) to convert PPi to ATP while ADP-glucose works as a substrate. Thus, the ADP-glucose pyrophosphorylase-based enzyme system according to the various embodiments is used to convert PPi to ATP optimally while avoiding the use of the sulfurylase and its substrate APS.

Advantages presented by the new enzyme system according to various embodiments of the invention relate to achieving a low background signal and producing high sample signals in the presence of a relatively large amount of luciferase. In various embodiments, the relatively large amount of luciferase may range, for example, from about 0.3 μg to about 3 μg. Accordingly, the sample amount of a nucleic acid (e.g., DNA) required for sequencing (e.g., pyrosequencing) using the new enzyme system according to various embodiments of the present invention can be significantly reduced as compared to the existing methods. Due to the low background, high sensitivity and specificity of AGPase-based reaction in converting PPi to ATP, the new enzyme system in various embodiments allows the sequencing to be carried out on a significantly reduced amount of the DNA sample with a well distinguishable signal for homopolymeric DNA regions. Hence, the AGPase-based enzyme system can be useful for analyzing clinical samples with very low DNA concentrations as well as developing high throughput allele frequency examination on large-scale pooled DNA samples. For example, according to various embodiments, the detectable amount of DNA can be about 0.025 pmol or less. For example, in various embodiments, about 0.025 pmol DNA may be detected in the presence of about 1.5 μg of luciferase. In various other embodiments, DNA samples having even lower amounts of DNA than 0.025 pmol may be detected, if relatively higher amounts of luciferase are applied in the sequencing system (e.g., about 3 μg of luciferase). Thus, the detectable sample concentration according to various embodiments can be, for example, about 6 times lower than the sample concentration which can be analysed using the existing ATP sulfurylase-based sequencing system, in which a generally acceptable sequencing quality may be obtained with a sample concentration of about 0.15 pmol to about 15 pmol of DNA. Furthermore, even at the lower limit of detection, the new enzyme system according to the various embodiments, works well for sequencing both mono- and homopolymeric regions (e.g., homopolymeric regions of up to about 10 consecutive nucleotides can be sequenced and distinguished). In contrast, the existing sequencing methods (e.g., an ATP sulfurylase-based sequencing system) appear to work for DNA amounts ranging from about 0.3 pmol to about 15 pmol. Therefore, the new enzyme system according to various embodiments provides more flexibility with regard to samples that can be analysed. Furthermore, lower amounts of the enzyme (AGPase) are required as compared with the existing pyrosequencing methods.

The new enzyme system (AGPase-based system), according to various embodiments, can be used to sequence more than about 70 bases of DNA, and as low as about 5% allele frequencies. The new enzyme system according to the various embodiments can yield a read-length of about 800 to 1000 base pairs. In contrast, the currently available sequencing methods such as the ATP sulfurylase-based sequencing system can yield a read-length of about 400 base pairs.

The new enzyme system according to the various embodiments can be incorporated into any system for analyzing a nucleotide molecule which comprises a conversion of PPi to ATP. Like with any existing enzymatic system, incorporation of the new enzyme system into a flow-through system is straight forward. Furthermore, because the new enzyme system allows for a lower limit of detection, a lower sensitivity camera may be sufficient in the particular analytical or sequencing system (e.g., pyrosequencing).

In various embodiments, a nucleotide degrading enzyme or a combination of nucleotide degrading enzymes may be used in addition to the new enzyme system. In various embodiments, the term "nucleotide degrading enzyme" relates to all enzymes capable of degrading nucleotides, including, for example, nucleoside triphosphates (NTPs), or a combination thereof. An example of the nucleotide degrading enzyme is apyrase. The nucleotide degrading enzyme may be included at various stages of the sequencing process, for example, during the polymerase reaction step by adding the enzyme to the reaction mixture at various points of the reaction. In various embodiments, the nucleotide degrading enzyme may be included in solution in a reaction mix for the polymerase reaction, or be immobilized on a solid support.

In various embodiments, PPi can be determined using methods known in the art. For example, luciferase and luciferin may be used to identify the release of PPi since the amount of light generated is proportional to the amount of PPi released, which is directly proportional to the amount of base incorporated. The amount of light can be determined by a light sensitive device (a detector, an imaging sensor).

The new enzyme system of the present invention may be used in a step-wise sequencing method, for example one that entails two steps, i.e., a polymerase reaction step followed by a detection step in which the release of PPi is detected. Alternatively, in other embodiments, the new enzyme system of the present invention may be used in a continuous method of sequencing which enables the sequencing reactions (base incorporation) to be continuously monitored in real time (e.g., by performing chain extension and detection). Thus, in various embodiments, the new enzyme system can be used for real time detection of nucleotide incorporation.

In various embodiments, the sample DNA (i.e., DNA template) may be single-stranded. The sample may be in solution or immobilized on a solid support. The sample DNA may be provided from any desired source of DNA including, for example, unamplified DNA, PCR or other amplified fragments, inserts in vectors or plasmids. In various embodiments, the amount of DNA available in a sample suitable for applications using the new enzyme system may range from about 0.025 pmol or less to about 0.2 pmol, from about 0.2 pmol to about 15 pmol, or from less than about 0.025 pmol to about 15 pmol. In various embodiments, the detectable sample amount may be modulated by varying the amount of luciferase in the particular sequencing application. For example, with about 0.5 µg of luciferase in the sequencing system, about 0.2 to about 15 pmol of DNA may be detected, or if a relatively higher amount of luciferase is used in the system (e.g., about 3 µg), about 0.025 pmol or less of DNA can be detected.

In various embodiments, including embodiments in which the new enzyme system is incorporated into the currently used sequencers (e.g. pyrosequencers), the solid support may comprise any solid support such as, for example, particles, fibers or capillaries (e.g, magnetic beads, capillaries made of agarose, cellulose, Teflon or polystyrene), or an array where the samples are distributed over a surface (e.g., a microfabricated chip). In various embodiments, the solid support may be further chemically modified to comprise functional groups or moieties for the attachment of, for example, primers or other reagents. In various embodiments, where accumulation of reaction byproducts may take place, washing of the sample (e.g., when the sample is immobilized on a support) may be performed.

In various embodiments, the efficacy (e.g., reaction efficiency) of the new enzyme system may be improved by including, for example, molecular crowders.

The various embodiments of the present invention in connection with the new enzyme system are further illustrated in detail in the Examples section.

Referring to FIG. 1, there is shown a schematic diagram of a sequencing system 10 according to an embodiment of the invention. In various embodiments, the sequencing system 10 is suitable for performing a sequencing analysis according to existing sequencing methods (e.g., ATP sulfurylase-based sequencing) or according to various embodiments described herein using the new enzyme system. In various embodiments the sequencing system 10 is a pyrosequencing system. The sequencing system 10 is suitable for performing de novo genome sequencing as is illustrated in the Examples section. In various embodiments, the sequencing system 10 is customizable and facilitates ultra-high throughput pyrosequencing. The sequencing system 10 comprises a reagent source 12, an imaging sensor 14, and a reaction platform 16. In various embodiments, the reagent source 12 is in fluid communication with the reaction platform 16 and can form a tight seal with the reaction platform 16. In various embodiments, the reaction platform 16 is mounted on the imaging sensor 14. In various embodiments, the reagent source 12 and the reaction platform 16 form a fluidic module of the sequencing system 10, and the imaging sensor 14 forms an imaging module. In various embodiments, the sequencing system 10 may further comprise a thermal subsystem (not shown) for modulating the temperature of the reaction platform 16, the imaging sensor 14, the reagents, or a combination thereof. Detailed embodiments of the sequencing system 10 are described in the Examples section.

In various embodiments, the reaction platform 16 comprises a plurality (e.g., millions) of reaction vessels (e.g., wells) disposed on, for example, a fiberoptic face plate. In various embodiments, the wells can be sized accordingly (e.g., each well may have a pico-liter capacity). The reaction platform 16 may be fabricated using standard semiconductor process technology.

In various embodiments, the reaction platform 16 can be integrated with the reagent source 12, the image sensor 14 for light (e.g., chemiluminescence) detection, or both. In various embodiments, the reaction platform 16 and the reagent source 12 may form an integrated and automated microfluidics-based system for sample preparation and reaction.

DNA sample preparation for short and long read sequencing strategies has become increasingly important, in particular for paired-end ditagging (PET) applications. PET is a powerful DNA preparation technique, which avoids positional ambiguities when mapping short single DNA to the entire genome and therefore increases the genome coverage. The existing PET protocols incorporate many critical steps spanning few days. Because PET is conducted in vitro, it is amenable to automation. In various embodiments, paired-end ditag library construction on a microfluidic platform can be integrated and automated in the sequencing system 10.

In various embodiments, the reaction platform 16 may be silicon-based or polymer-based. A silicon-based reaction platform 16 presents several advantages. For example, a silicon-based enzymatic microreactor for PET library construction can involve small reagent consumption, have good thermal conductivity, and does not entail using magnetic beads. The main disadvantage of using the silicon based microreactor (e.g., a micro-PCR chip) for PET Library construction relates to the limitation of the dimensions of the chip (e.g. a volume of about 10-20 µL). In various embodiments, the surface of the reaction platform 16 may be chemically modified. In various embodiments, chemical modification may comprise direct functionalization on the surface of the reaction platform 16 (e.g., functionalization directly on the silicon surface). For example, such functionalization directly on the reaction platform 16, such as the silicon surface, may comprise first immobilizing biotin molecules followed by streptavidin molecules, which allows for direct attachment of the biotinylated circularized PET molecule to the surface.

In various embodiments, a polymer-based reaction platform 16 may entail a modular approach where the PET can be performed on a disposable plastic chip consisting of different modules. In various embodiments, such modules can include enzymatic, silica purification, resuspension, vortexing, electrophoresis, magnetic purification modules or a combination thereof. In various embodiments, the analytical aspects can include a permanent module consisting of fluidic, electrical, vibration, magnetic, thermal modules or a combination thereof.

Both silicon-based and polymer-based approaches to automate and integrate different PET steps may be performed using the reaction platform 16 according to various embodiments of the present invention.

In various embodiments, after the sample preparation, amplification or a combination of sample preparation and amplification, an individual bead with a single copy of a DNA fragment can be dispensed into a single well of the fiberoptic faceplate. The detection enzyme (e.g., luciferase) can be immobilized on smaller beads and remain associated with the wells throughout the process. Packing beads can fill the remaining part of the wells. Various types of beads may be used in various embodiments, and the type of bead may be tailored to a particular process. For example, the type of beads may be selected so as to maximize the. DNA attachment onto the beads. An example of one type of beads suitable for use in various embodiments of the present invention is porous silica beads. Such beads present higher surface-to-volume ratio and a suitable DNA binding capacity. Signals from porous silica beads increase by about four times as compared to signals obtained using standard sepharose beads (assuming both types of beads are of similar sizes).

In various embodiments, the pyrosequencing chemistry may be tailored to achieve a desired result. For example, the pyrosequencing chemistry may be modulated by optimizing the pyrosequencing chemistry in new domains. In various embodiments, concentrated nucleotides may be used. In various embodiments, with the exception of DNA and enzymes (which may be tagged on beads), all reagents can be water-based with minimal amounts of nucleotides and other chemicals. In various embodiments, the concentrated nucleotides may be used in small vials and be integrated into a flow scheme where the nucleotides and other reagents mix together with deionized water before getting dispensed into the sequencing chamber of the reaction platform 16. Such an approach has the advantage of reducing the size of the reagent cartridge.

In various embodiments, the image sensor 14 may comprise any type of sensor such as, for example, a CCD type sensor or a CMOS type image sensor. The selection of a suitable image sensor 14 may be tailored to the particular sequencing parameters and desired sensitivity as well as can involve other considerations such as cost. For example, the use of the CMOS type image sensor in the various embodiments of the sequencing system 10 provides comparable performance to CCD image sensors at a fraction of a cost. In addition, the CMOS type image sensor offers easy system integration and on-board signal conditioning electronics. Other advantages of the CMOS type image sensor include higher read-length, label-free, real-time pyrosequencing, and low initial instrumental and reagent costs. In various embodiments, a region of the sequencing system 10 as small as about 100 $mm^2$ is capable of sequencing more than one million bases.

In various embodiments, the image sensor 14 such as the CMOS image sensor can be used in combination with a photomultiplier tube and a fiberoptic faceplate with millions of etched wells (i.e., a picotiterplate which is a much deeper version of the traditional microtiterplate). Various associated parts such as, for example, multiposition valve, peristaltic pump, sensor controller can be integrated inside a light-tight enclosure.

In various embodiments, several strategies can be implemented to generate wells on a fiberoptic faceplate. For example, such wells may be commercially available by etching each individual fiber. They can be, however, expensive (about 500 USD per piece) and are disposable. In various embodiments, to make the faceplate reusable, the wells may be photolithographically fabricated on the faceplate. Such fabrication may, for example, entail using a mask and a negative photoresist (SU-8). In yet other embodiments, the faceplate itself may be used as a mask and a positive photoresist may be used to generate wells on the faceplate. Such a method can allow fabrication of the maximum number of wells, which leads to more DNA beads per plate.

Also, the faceplate can be reused. This method can address key important issues of increasing throughput (maximum number of wells per faceplate) while reducing the cost (e.g., by reusing the faceplate).

In various embodiments, the image sensor 14, such as the CMOS image sensor, may be optimized for the particular application. In various embodiments, optimization may include, for example, dark-current measurements, temperature stability tests, integration time test or a combination thereof. Furthermore, in various embodiments, the image sensor 14 can be cooled down by using, for example, a thermoelectric cooler, and the GUI for image-capture and signal-to-background modification in real-time may be upgraded.

In various embodiments, the sequencing system 10 of the present invention provides several advantages. For example, one advantage relates to the cost of the reaction platform 16 alone or in combination with the reagent source 12, which in various embodiments can be automated and integrated. In comparison to the present cost- and time-consuming systems, the sequencing system 10 of the present invention can reduce the sequencing time to a few hours and the cost to a few hundred dollars. Another advantage relates to the sequencing reagent cost. In contrast to currently available sequencing systems, the sequencing system 10 is capable of achieving the goals of about 1000 USD per genome. The sequencing time needed to perform sequencing is yet another advantage of the sequencing system 10, which can achieve sequencing of a few genomes per day.

In various embodiments, the sequencing system 10 may incorporate electro-guided well filling and reagent dispensation in place of pressure-driven flow.

This can be achieved by leveraging the negative charge on DNA and applying positive charges to complete sequencing runs.

A further advantage of the sequencing system 10 relates to the instrument cost. Compared to conventional techniques, the sequencing system 10 has a lower platform cost, which in various embodiments can range from about 30000 USD to about 15000 USD. Yet another advantage of the sequencing system 10 according to the various embodiments relates to the targeted and customized sequencing (e.g., its pluggable-and-playable trait). Based on the sample size and user's requirements, the sequencing system 10 can sequence data ranging from few kilobases to few hundred megabases (e.g., about 60 megabases per run, or about 3 billion bases per run). In contrast, the existing sequencing instruments are time consuming and costly even when a small sample size is analyzed.

Adaptability of the sequencing system 10 according to the embodiments of the present invention allows the sequencing system 10 to be used and accessible not only to the big sequencing centers but also to smaller laboratories. The sequencing system 10 according to the various embodiments of the present invention can be used to sequence, for example, bacteria and yeast, and targeted genes with mRNA.

According to various embodiments, several modifications may be performed to the sequencing system 10. For example, in various embodiments, the well-loading capacity may be increased, which may range, for example, from about 30% to more than about 80% by, for example, optimizing the centrifugation process or by electro-guided well filling. In various embodiments, the run-time may be lowered by having a flow under electric field. In various embodiments, the CMOS sensor may be optimized by cooling it below 0° C. In various embodiments, the reagents may be kept cool for the entire sequencing process. In various embodiments, the enzymatic reaction may be optimized by increasing the reaction-chamber temperature. In various embodiments, the light guidance from fiberoptic faceplate to CMOS sensor may be optimized by optical simulation. Furthermore, one or more of the above modifications may be used in combination with the new enzyme system according to the various embodiments to achieve increased read-length and detection limit.

In various embodiments, the sequencing system 10 provides a pluggable-and-playable system based on the sample size, ultra-high sensitive image-sensor based on standard microfabrication techniques which are inexpensive, customizable and low-noise, cost of less than about 20,000 USD, and an integrated reaction platform 16 which, in various embodiments, is micro-fluidics based and low cost.

EXAMPLE 1

Reagents

AGPase (3.6 U/mg protein) was obtained from a private source. D-Luciferin, ADP-glucose (ADPGlc), phosphoenolpyruvate trisodium (PEP), pyrophosphate decahydrate (PPi), Poly (vinylpyrrolidone) (PVP), apyrase and bovine serum albumin (BSA) were purchased from Sigma (St. Louis, Mo.). ATP Sulfurylase was purchased from Merck (Whitehose station, USA). Adenosine 5'-phosphosulfate (APS) and deoxynucleotide (dNTPs) were purchased from MyChem (San Diego). Single-stranded DNA binding protein (SSB) was purchased from GE Healthcare (Uppsala, Swdedn) while Exo⁻ Klenow was purchased from NEB (Massachusetts). Luciferase was purchased from Promega (Madison). PyroGold reagents were purchased from Qiagen (Uppsala, Swdedn). Plasmid pUC19 and PCR amplification master mix were purchased from Fermentas (Burlington, Canada). Streptavidin-coated Sepharose™ high performance, beads were purchased from GE Healthcare (Uppsala, Sweden).

Oligonucleotides

The oligonucleotide sequences shown in Table 1 were synthesized and HPLC purified by Sigma.

TABLE 1

| Name | Nucleotide sequence (5' 3') |
|---|---|
| SG_seq | GGACTATAAAGATACCAGGCGTT (SEQ ID NO: 8) |
| SG_12 | Biotin-TAACCGGTACGAACGCCTGGTATCTTTATAGTCCATC (SEQ ID NO: 9) |
| SG_122 | Biotin-ATCAAGGCCTTATGCTTCCAAGGAGTCTACGAACGCCTGGTATCTTTATAGTCCATC (SEQ ID NO: 10) |
| SG_repeated C | Biotin-CTGCGGGGGAAGGGGGCAGGGGTGCGGGTAGGAGTAAACGCCTGGTATCTTTATAGTCCA (SEQ ID NO: 11) |
| SG_10T | Biotin-ACGAGAAAAAAAAAAGATAACAACGCCTGGTATCTTTATAGTCCA (SEQ ID NO: 12) |
| pUC19_F | Biotin-ATAACTACGATACGGGAGGG (SEQ ID NO: 13) |
| pUC19_R | GCTATGTGGCGCGGTATTAT (SEQ ID NO: 14) |
| pUC19_seq | CTTCCGGCTGGC (SEQ ID NO: 15) |
| Homo_1 seq | GCGCGGTATTATCCC (SEQ ID NO: 16) |
| Homo_2 seq | GATAACACTGC (SEQ ID NO: 17) |
| SNP_C | AACGACCCGGCCGAACGCCTGGTATCTTTATAGTCCA (SEQ ID NO: 18) |
| SNP_T | AACGACCCGGCCAAACGCCTGGTATCTTTATAGTCCA (SEQ ID NO: 19) |

In Table 1, overlaps between sequencing primer SG_seq and Oligos SG_12, SG_122, SG_repeated C, SG-10T, SNP_C and SNP_T are underlined.

Template DNA Preparation

The template DNA was obtained by PCR reaction with primer pair of pUC19_F and pUC19_R to generate a 558 by DNA fragment. The amplification was carried out on a Bio Rad thermo Cycler PCR system (CA, USA) with the following protocol: denaturing at 95° C. for 30 s, followed by 30 thermal reaction cycling (95° C. for 30 s, 60° C. for 30 s and 72° C. for 45 s). After 30 thermal cycle reactions, the product was incubated at 72° C. for 5 min to ensure the complete extension of the amplified DNA fragment. Streptavidin coated-sepharose beads were used to immobilize biotinylated DNA oligos. The immobilization was performed by incubating the mixture of DNA and beads in binding buffer (10 mM Tris-HCl, 2 M NaCl, 1 mM EDTA, 0.1% Tween 20, pH 7.6) at room temperature for 30 min with gentle shaking. Single-stranded pUC19 DNA fragment was then obtained using vacuum preparation protocol according to the manufacturer's instructions.

Annealing of sequencing primer (SG_seq) with different biotinylated DNA oligos (SG_12, SG_122, SG_10T, SG_repeated C, SNP_C and SNP_T) or Homo_1 seq, Homo_2 seq, and pUC19_seq with single-stranded pUC19 DNA fragment was carried out in the annealing buffer (20 mM Tris-Acetate, 2 mM MgAc$_2$ pH 7.6) at 95° C. for 5 min and then cooled down to room temperature gradually. Following which, the double-stranded DNA samples were sent for sequencing.

To prepare the DNA samples for allelic frequency determination, two synthesized DNA oligos (SNP_C and SNP_T with one nucleotide difference in the sequence) were mixed at different proportions before annealing with the sequencing primer SG_seq.

Preparation of ADPGlc-AGPase Based Sequencing Solution

In an embodiment of the invention, primed DNA sample was added to the final volume of 40 µl pyrosequencing reaction mixture containing 60 mM Tricine (pH 7.75), 0.5 mM EDTA, 5 mM magnesium acetate, 1 mM dithiothreitol, 100 pg D-luciferin, 0.1% bovine serum albumin, 0.4 mg/ml polyvinylpyr-rolidone (360,000), 2.5 mM ADP-Glucose, 0.5 µg of E. coli single-stranded DNA-binding protein, 5 U exonuclease-deficient (exo⁻) Klenow DNA polymerase, 40 mU apyrase, 2.5 mU AGPase and an appropriate amount of luciferase.

Preparation of the Conventional APS ATP Sulfurylase-Based Sequencing Solution

For comparison, the buffer condition for the conventional APS-ATP Sulfurylase system was the same as that for the ADPGlc-AGPase enzyme system according to an embodiment of the invention. Primed DNA sample was added to the final volume of 40 µl pyrosequencing reaction mixture containing 60 mM Tricine (pH 7.75), 0.5 mM EDTA, 5 mM magnesium acetate, 1 mM dithiothreitol, 100 µg D-luciferin, 0.1% bovine serum albumin, 0.4 mg/ml polyvinylpyr-rolidone (360,000), 5 µM APS, 0.5 µg of E. coli single-stranded DNA-binding protein, 5 U exonuclease-deficient (exo⁻) Klenow DNA polymerase, 40 mU apyrase, 15 mU ATP Sulfurylase and an appropriate amount of luciferase.

Preparation of AMP-PPDK Based Sequencing Solution

Primed DNA sample was added to the final volume of 40 µl pyrosequencing reaction mixture containing 60 mM Tricine (pH 7.75), 0.5 mM EDTA, 5 mM magnesium acetate, 1 mM dithiothreitol, 100 µg D-luciferin, 0.1% bovine serum albumin, 0.4 mg/ml polyvinylpyr-rolidone (360,000), 0.08 mM PEP, 0.4 mM AMP, 0.5 µg of E. coli single-stranded DNA-binding protein, 5 U exonuclease-deficient (exo⁻) Klenow DNA polymerase, 40 mU apyrase, 0.6 U PPDK and an appropriate amount of luciferase.

Pyrosequencing

Pyrosequencing was carried out on PyroMark Q96 ID system (Qiagen). After an initial dispensation of enzyme and substrate mixes, the sequencing procedure in this embodiment was accomplished by stepwise elongation of the primer strand through iterative additions of deoxynucleoside triphosphates and simultaneous detection of resulting bioluminescence emission.

Optimization of Sequencing Reactions in AGPase-Based Pyrosequencing System

Figure 2A:
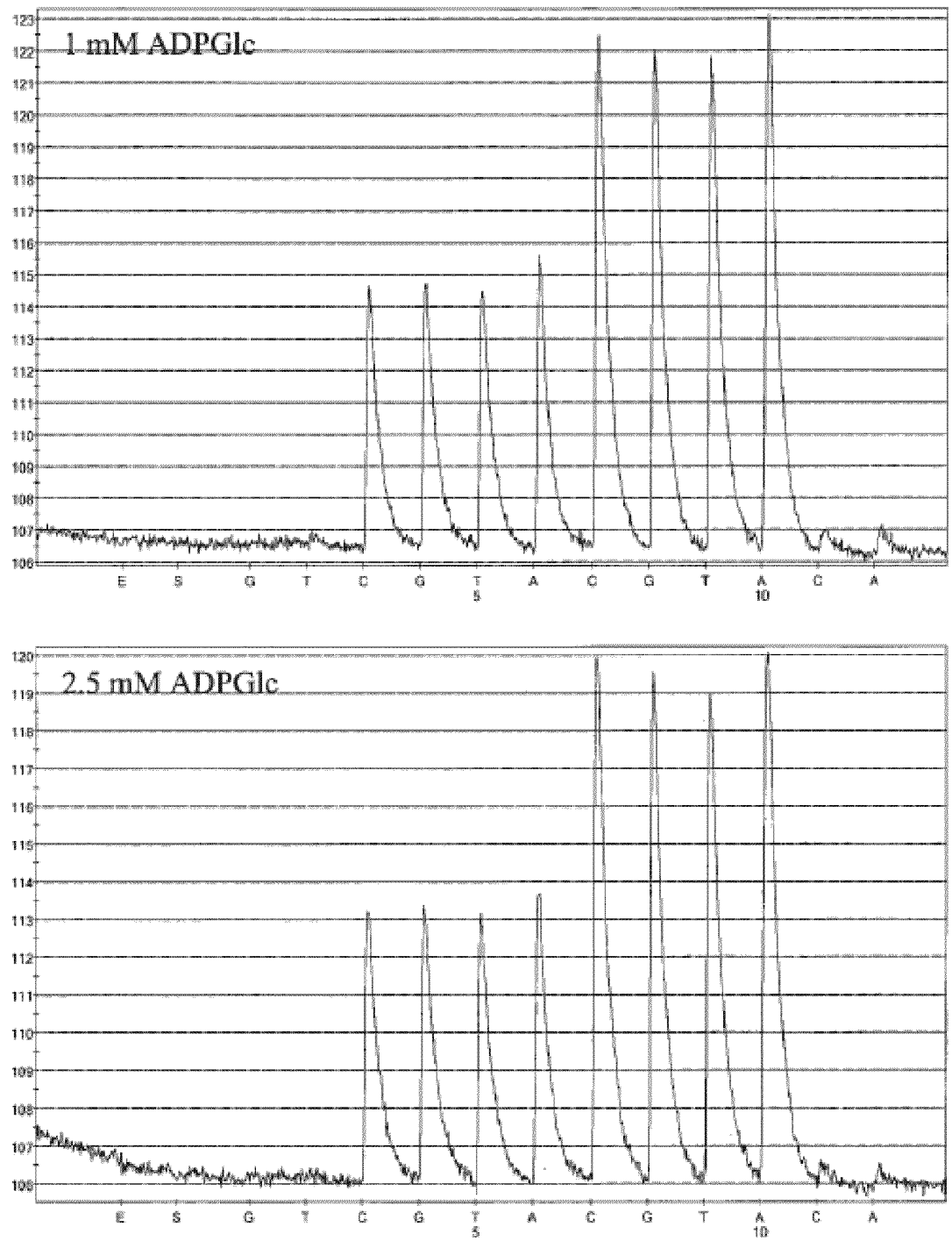
FIG. 2A illustrates pyrosequencing with various amounts of ADPGlc (1-5 mM)
Figure 2A:
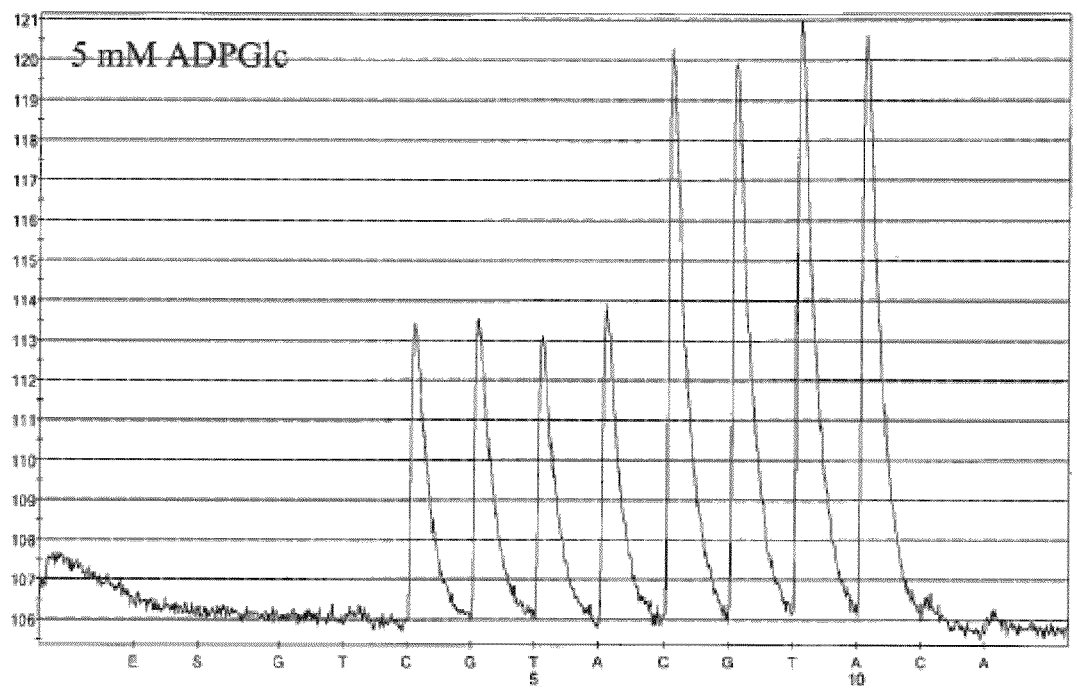

In the AGPase-based pyrosequencing system according to an embodiment of the invention, ADPGlc was used as substrate in the reaction converting PPi to ATP. As shown in FIG. 2A, there was no significant change in signal intensities with ADPGlc at a range of about 1-5 mM. Therefore, about 2.5 mM of ADPGlc was selected for various subsequent experiments.

Figure 2B:
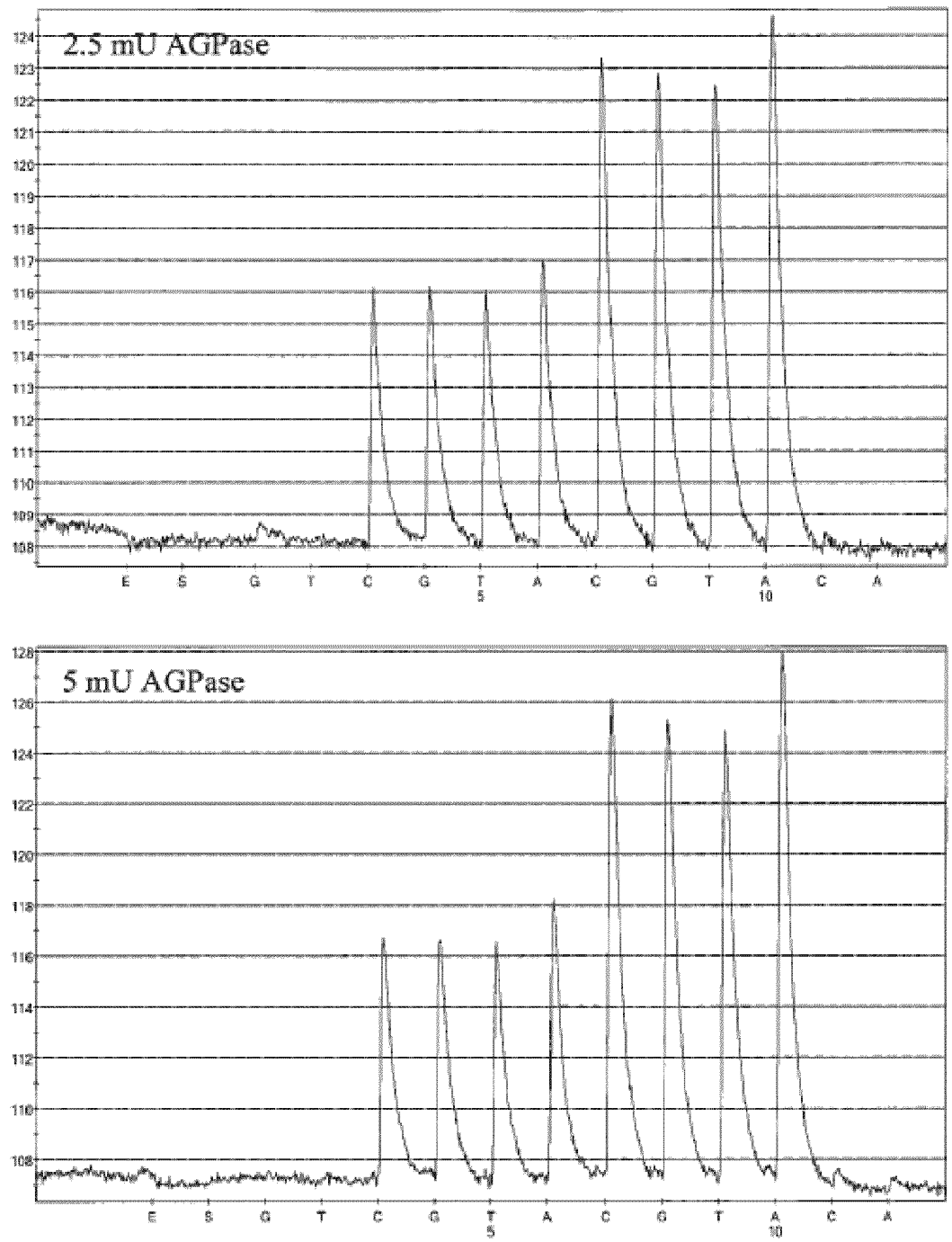
FIG. 2B llustrates pyrosequencing with various amounts of AGPase (2.5 mU, 5 mU, 7.5 mU)
Figure 2B:
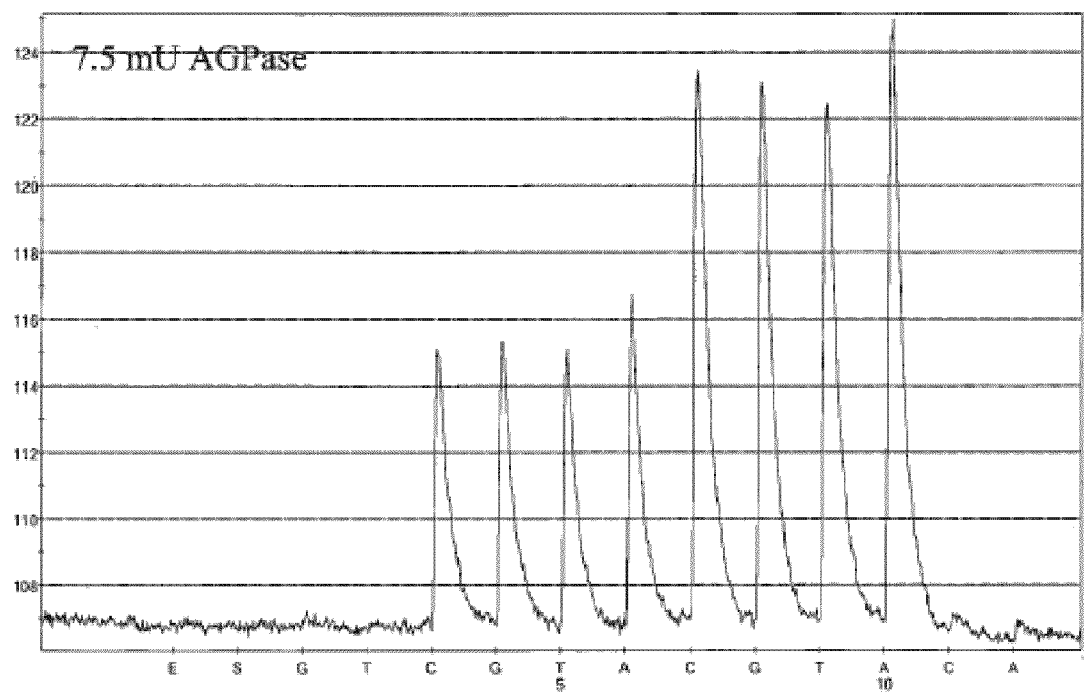

The second reaction in the AGPase-based pyrosequencing technology according to an embodiment of the present invention, namely the production of ATP from PPi released upon DNA polymerization, is catalyzed by AGPase: PPi+ADP-Glc $\leftrightarrow$ ATP +Glc-1-phosphate. This reaction has been widely described in many bacterial extracts or plant tissues. The enzymatic reaction takes place in the presence of a divalent metal ion, Mg$^{2+}$, and it is freely reversible in vitro, with an equilibrium close to 1. FIG. 2B demonstrates the sequencing signal obtained from the AGPase-based system according to an embodiment of the present invention with various amounts of AGPase. The data suggest that as low as about 2.5 mU of AGPase could successfully convert PPi generated from about 1 pmol of DNA template to ATP.

In pyrosequencing, apyrase is used for degradation of unincorporated nucleotides and excess ATP between base additions. Insufficient or excess apyrase activity can cause plus or minus frameshift of a sequencing profile.

Figure 2C:
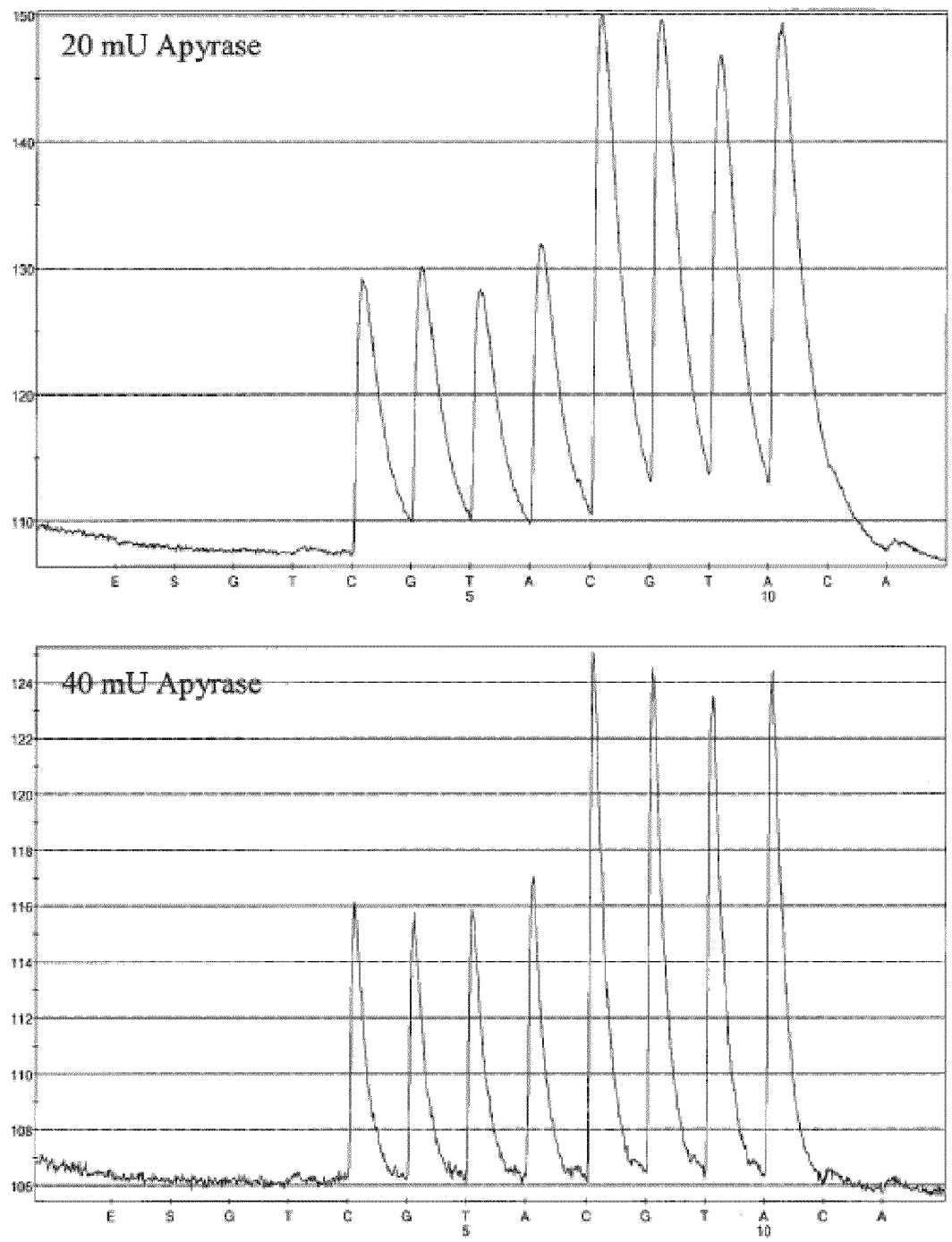
FIG. 2C illustrates pyrosequencing with various amounts of apyrase (20 mU, 40 mU, 60 mU)
Figure 2C:
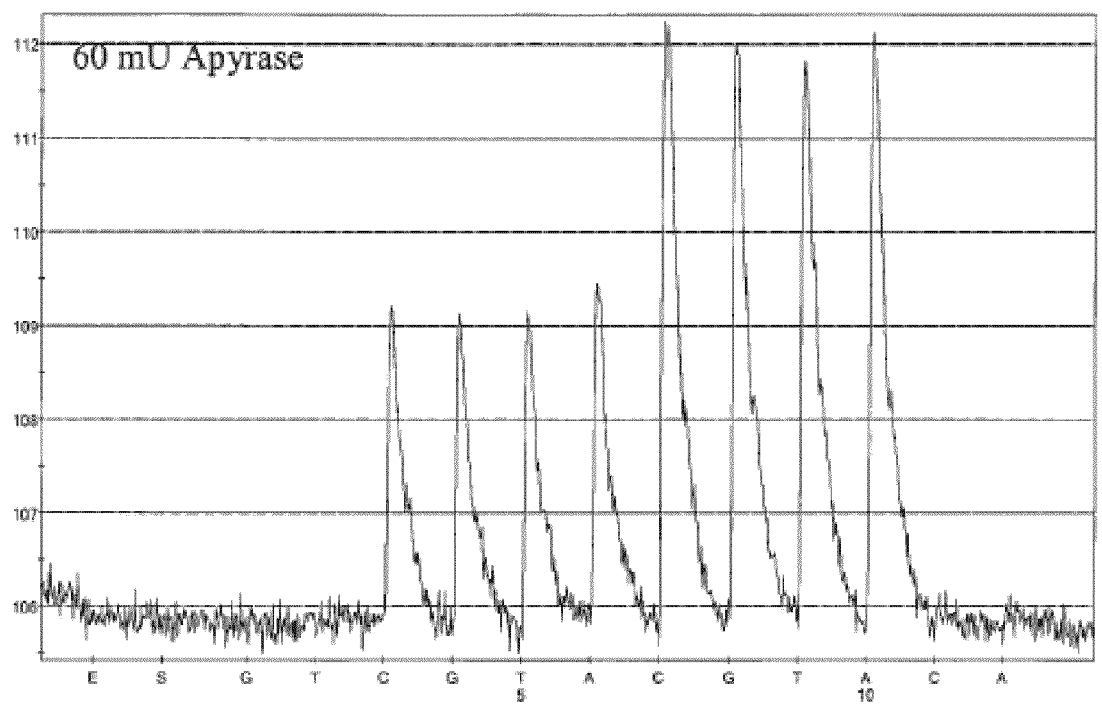

The frame shifts can subsequently result in uncertain or erroneous interpretation of the programs. Hence, it is important to select an appropriate concentration of apyrase. Pyrograms obtained with different amount of apyrase are shown in FIG. 2C. It is demonstrated in FIG. 2C that although higher sequencing signals were detected with lower amount (20 mU) of apyrase, the signals could not reach baseline before the appearance of next sequencing peak indicating the accumulation of ATP between cycles. In contrast, when a higher amount of apyrase (60 mU) was applied, the sequencing peak height decreased significantly. This might be explained by nucleotide degradation by excess amount of apyrase occurring faster than nucleotide incorporation by the DNA polymerase. Therefore, 40 mU of apyrase was selected in the AGPase-based pyrosequencing system according to an embodiment of the present invention to achieve the yield of primer-directed incorporation as close to about 100% as possible.

Figure 2D:
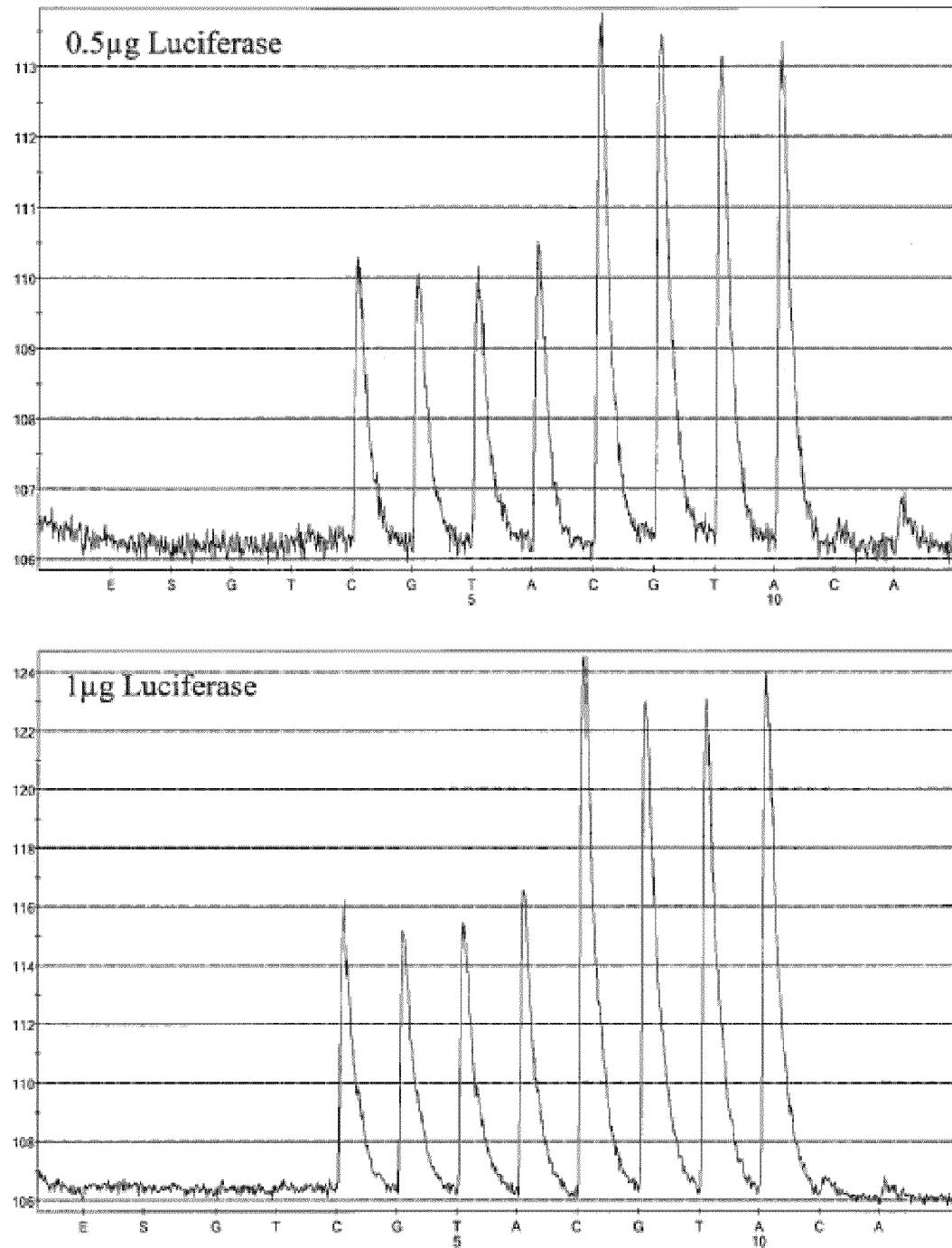
FIG. 2D illustrates pyrosequencing with various amounts of luciferase (0.5 μg, 1 μg, 1.5 μg). The oligo sequence order: CGTACCGGT-TAA(SEQ ID NO:1)
Figure 2D:
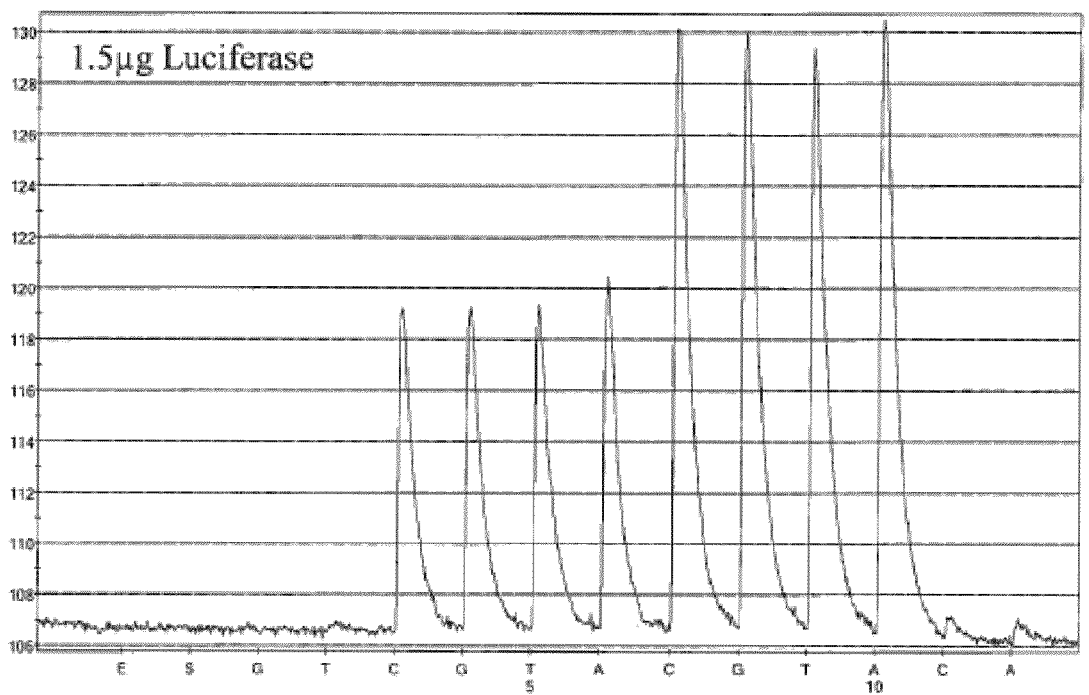

In the AGPase-based pyrosequencing system according to an embodiment of the present invention with appropriate amount of apyrase, upon successful polymerization by DNA polymerase and generation of ATP by AGPase, the height of the signals is determined by the activity of luciferase. As shown in FIG. 2D, higher signal intensity was detected with increasing amount of luciferase. In addition, the AGPase-based system according to an embodiment of the present invention showed comparable luminescence signals (FIG. 3) with constant low background regardless of the amount of luciferase (FIG. 4). The data indicate that higher amount of luciferase could be employed in AGPase-based pyrosequencing system according to an embodiment of the present invention to increase the detection sensitivity especially for those DNA samples with very low concentration.

Base Calling in the Homopolymeric Stretch

In a DNA template, the homopolymeric regions are the regions containing multiple simultaneous copies of a single base (A, C, G or T). During the pyrosequencing, homopolymeric regions can reduce synchronized extension and synthesis of the DNA strand and cause non-uniform sequence peak heights, affecting the read-length and possibly causing sequence errors.

Figure 5A:
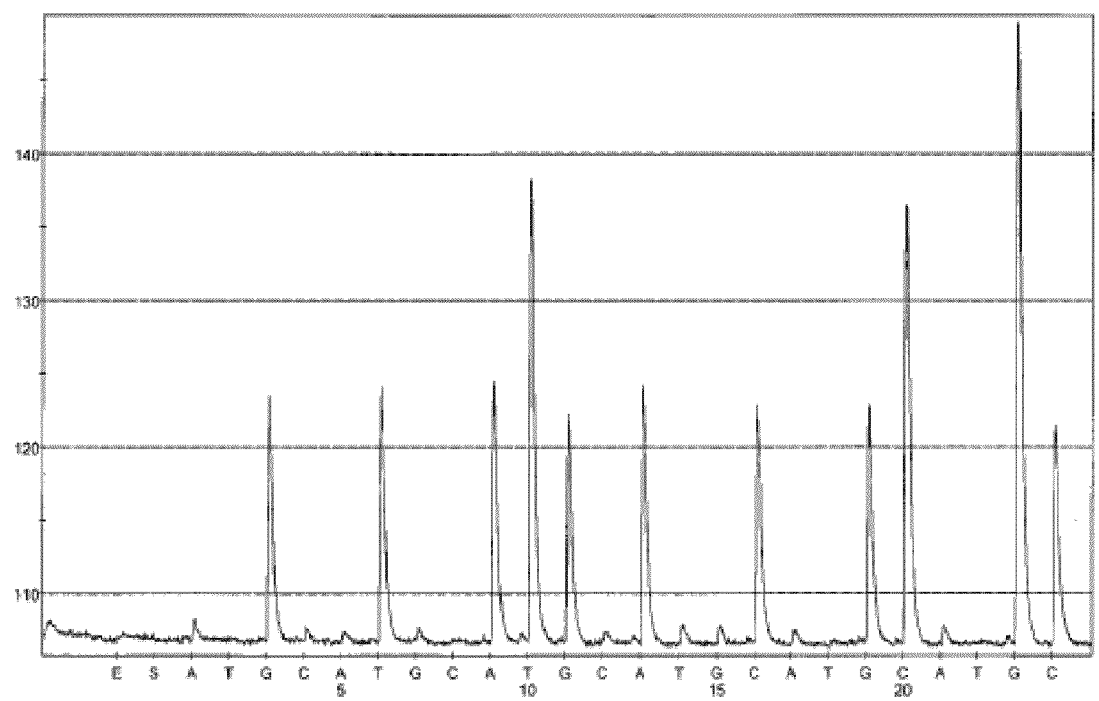
FIGS. 5A and 5B show that the templates are single-stranded PCR products of pUC19.
Figure 5B:
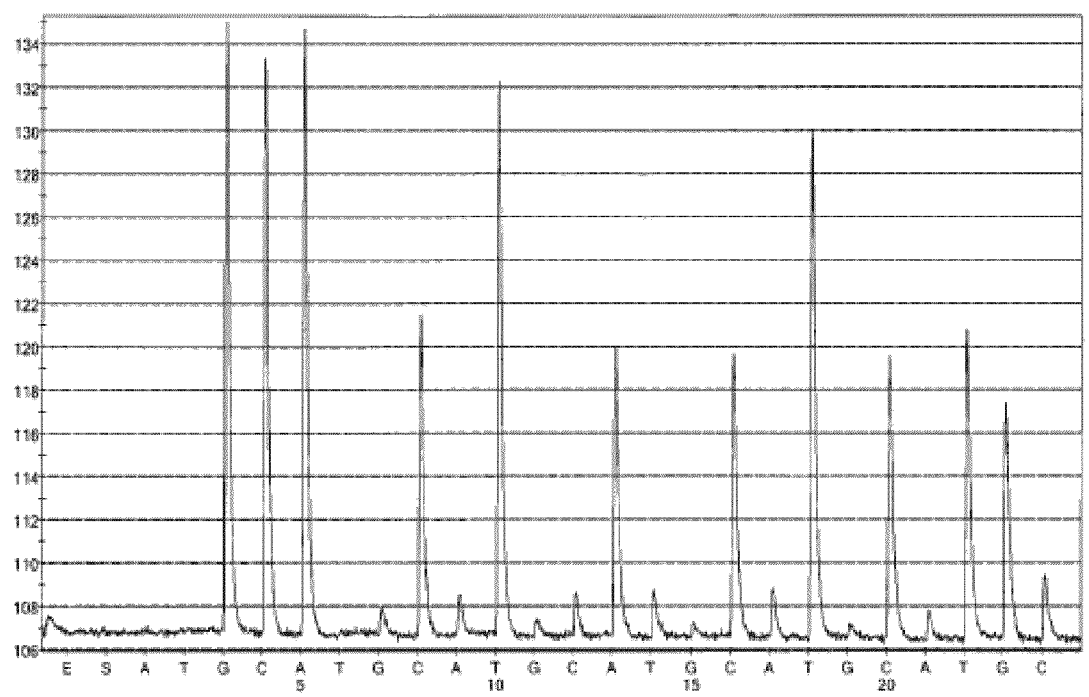
Figure 5C:
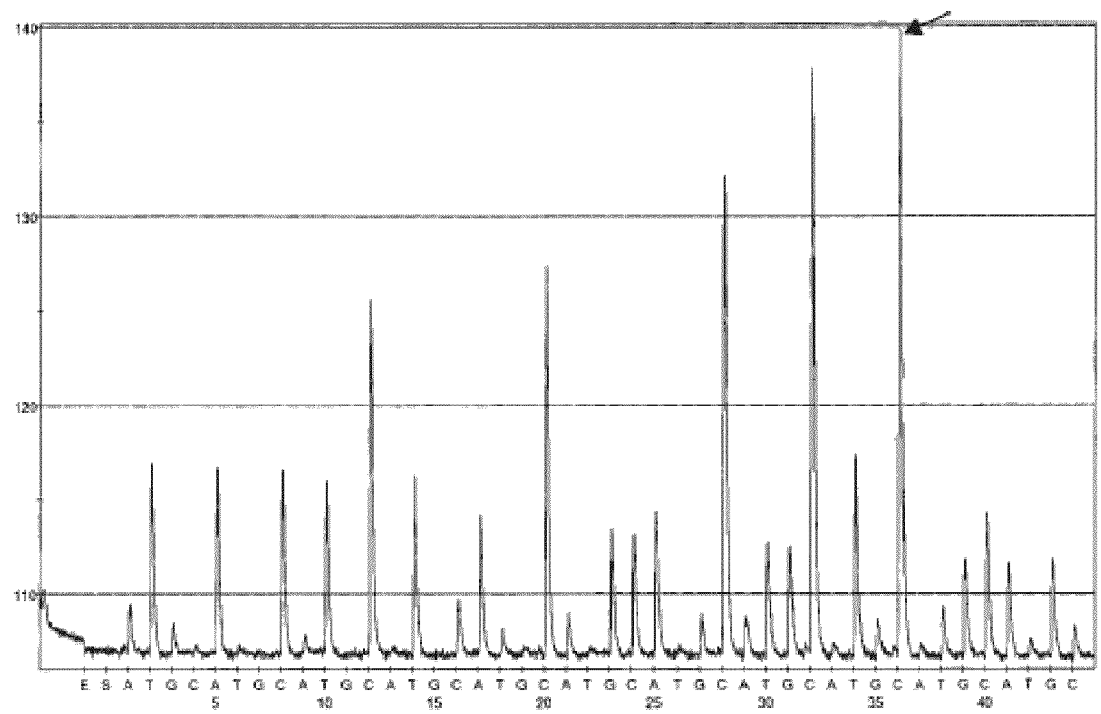
FIGS. 5C and 5D show that the templates are synthesized oligos. Oligo sequence for FIG. 5A: GTATTGACGC-CGGGC(SEQ ID NO:2),for FIG. 5B, GGCCAACTTACT-TCTG(SEQ ID NO:3), for FIG. 5C, TACTCCTACCCG- CACCCCTGCCCCCTTCCCCCCGC AG(SEQ ID NO:4), and for FIG. 5D, GTTATCTTTTTTTTTTCTCGT(SEQ ID NO:5). The dNTP dispensing order was A>T>G>C.
Figure 5D:
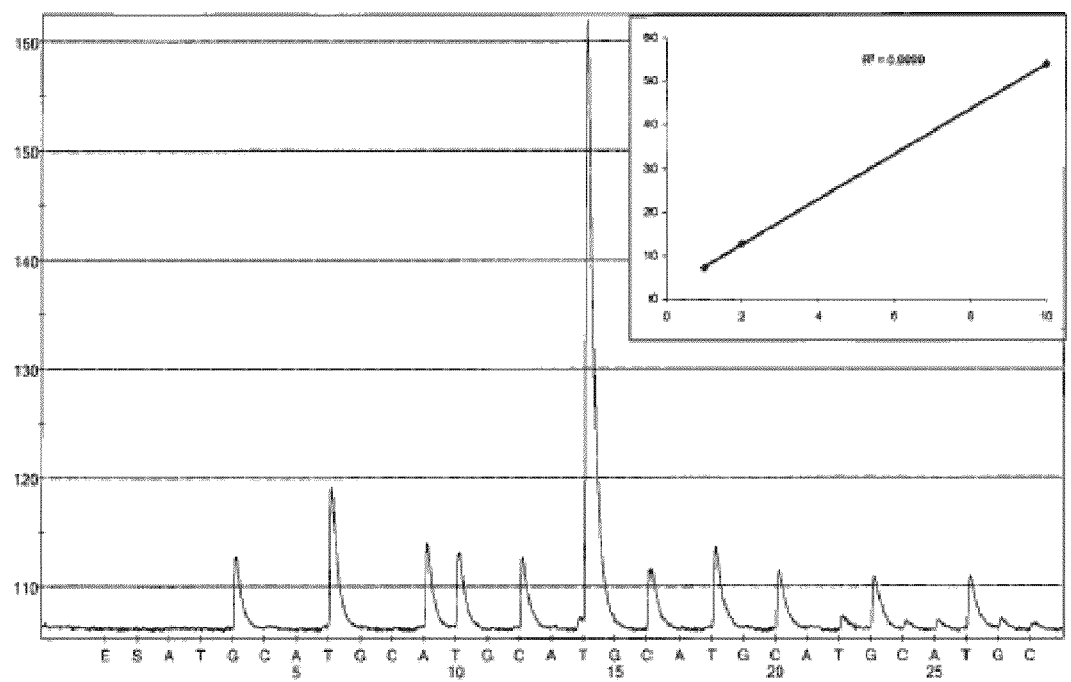

Therefore, the determination of the identical base number in the homopolymeric region during pyrosequencing is important. The number of incorporated bases in DNA templates prepared from pUC19 as well as synthesized oligo DNAs with different homopolymeric stretches (SG_repeated C and SG_10T) was investigated quantitatively. The programs shown in FIG. 5 indicate that signal intensities are aligned well to the number of incorporated bases in various homopolymers. In FIG. 5C, the peak intensity of C (marked by an arrow) was not in proportion to six Cs, though it was higher than that for five Cs. This is in agreement with the previous finding that the light signal intensity is not exactly proportional to the amount of PPi released, especially when the homopolymeric region has more than five bases. However, through using specific software algorithms to compensate the signals, the correct number of incorporated nucleotides may be elucidated. As shown in FIG. 5D, based on the signal intensities, the AGPase-based pyrosequencing system according to an embodiment of the invention can determine as many as 10 identical bases incorporated at a time.

Long-Read DNA Sequencing

Long-base reading is desirable in applying pyrosequencing to genome sequencing, microbial typing, and resequencing. The performance of the AGPase-based pyrosequencing system according to an embodiment of the invention for long-base sequencing was investigated.

Figure 6:
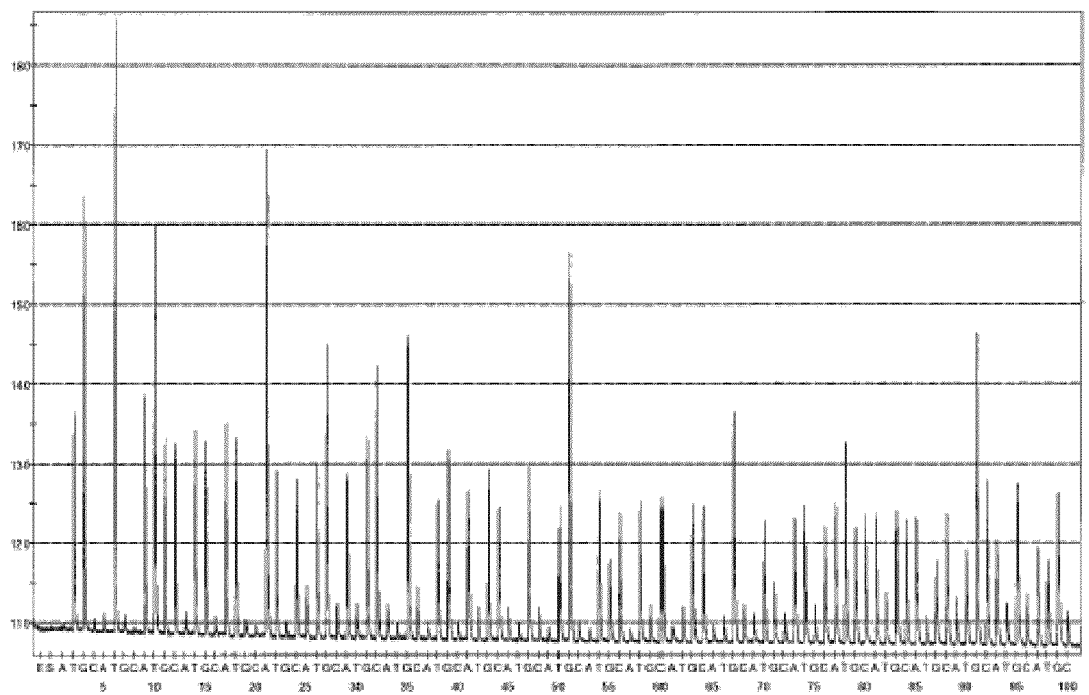
FIG. 6 shows a long-base read pyrogram of 1 pmol single-stranded pUC19 PCR product. The oligo sequence order: TGGTTTATTGCTGATAAATCTGGAGCCG-GTGAGCGTGGG TCTCGCGGTATCATTGCAG-CACTGGGGCCAGATGG(SEQ ID NO:6). The dNTP dispensing order was A>T>G>C.
Figure 7A:
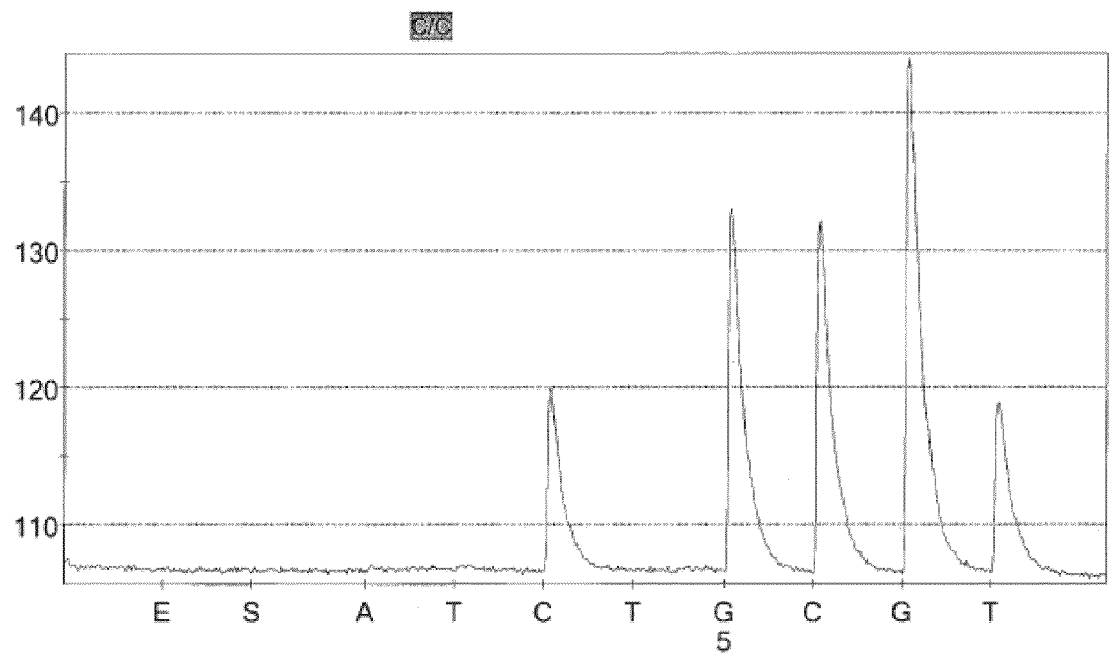
Figure 7B:
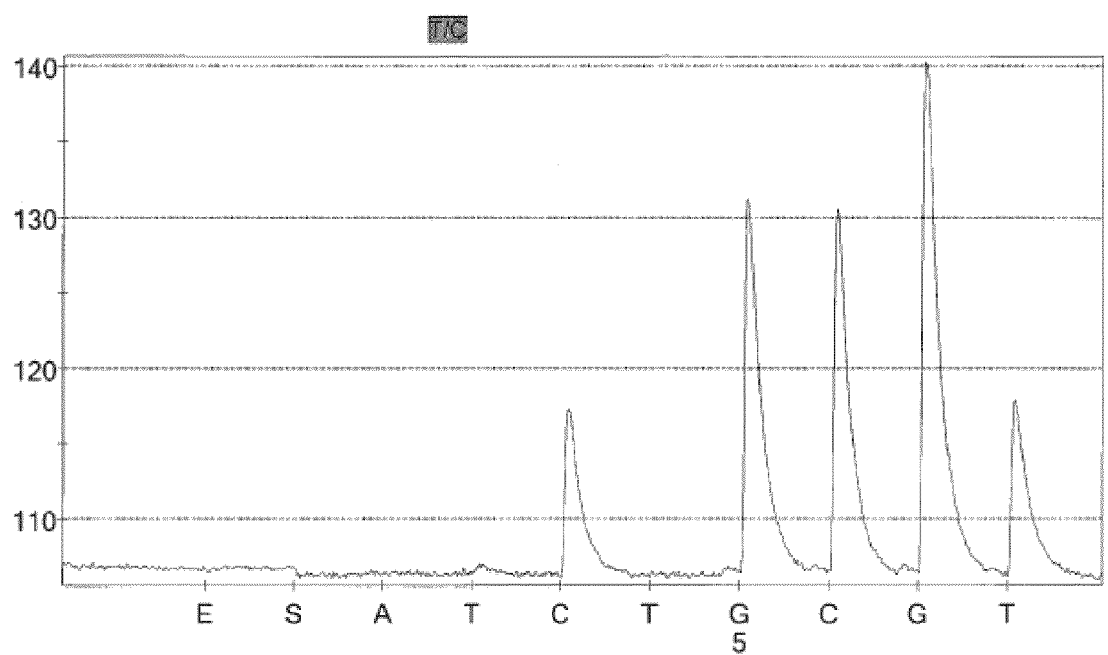
Figure 7C:
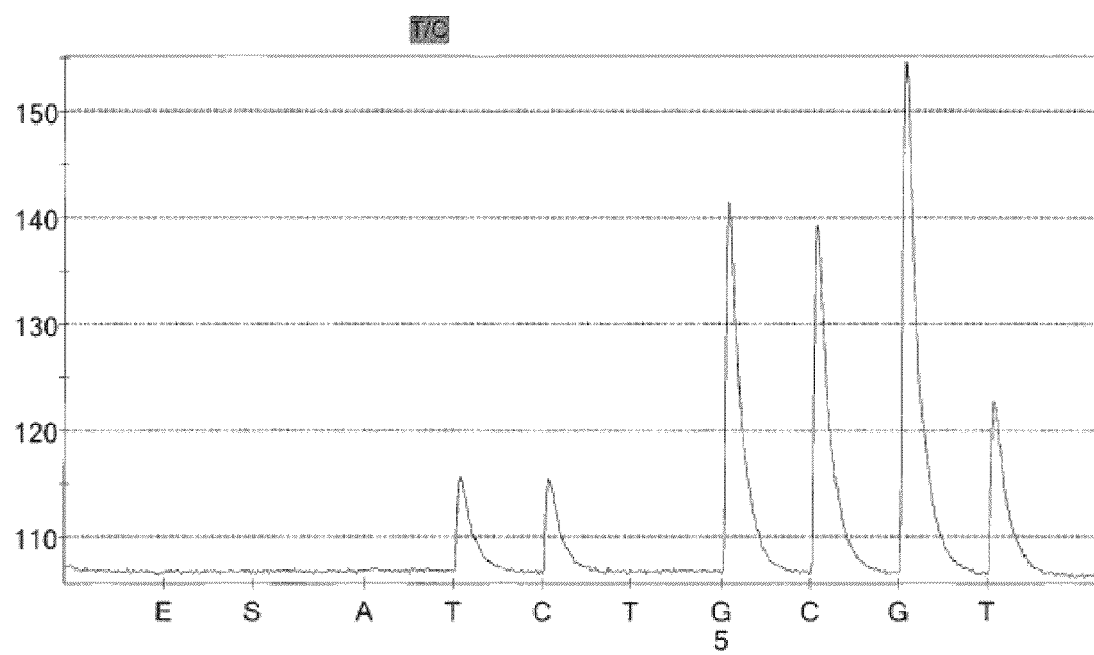
Figure 7D:
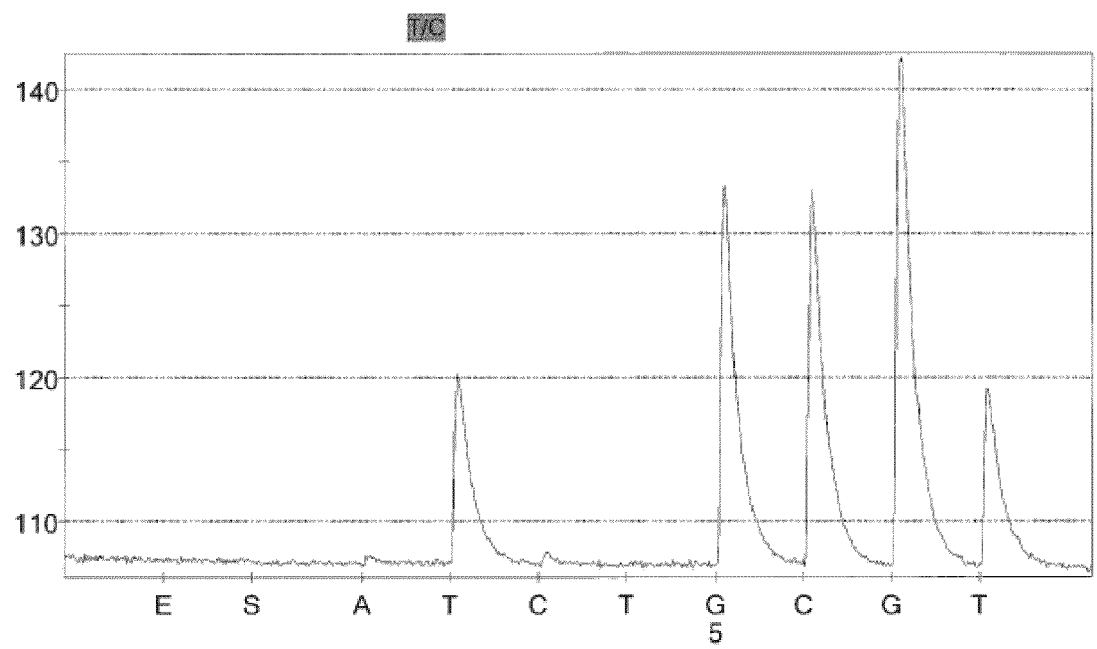
Figure 7E:
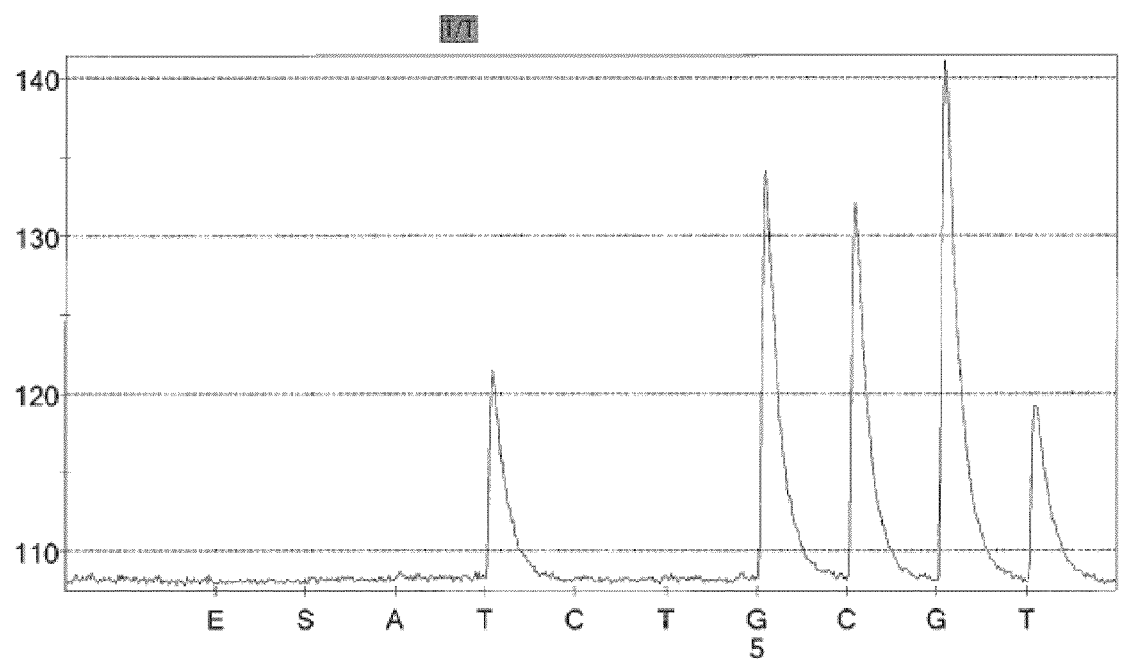

As shown in FIG. 6, the signal intensities to the incorporated base decreased gradually with increasing read length. The decreasing signal intensities in the long-base region may be, for example, from the exonuclease activity of DNA polymerase causing primer degradation in the long read sequencing. In addition, the accumulation of byproducts during sequencing and the dilution effect produced by the continuous addition of nucleotides may reduce the efficiency of the enzymes in the pyrosequencing reaction. However, besides the decreasing signal intensity, 75 bases can be successfully sequenced and analyzed using the AGPase-based pyrosequencing system according to an embodiment of the invention with about 98.7% base call accuracy as is illustrated in FIG. 6.

Allele Frequency Determination

Genetic variation is the basis for human diversity and plays an important role in human diseases. Two major types of variants are known in the human genome: tandem repeats of single sequences such as microsatellites and single nucleotide polymorphisms (SNPs). SNPs are much more abundant than microsatellites and some SNP mutations may be causative of the disease phenotypes. Therefore SNPs examination can be potentially very powerful in detecting linkage disequilibrium around disease loci.

In pyrosequencing, PPi is released as a result of the nucleic acid polymerization step, and the amount of PPi is directly proportional to the amount of DNA and number of incorporated nucleotides, but not the type of incorporated nucleotides. The quantitative data generated during pyrosequencing make this technique suitable for the studies of allelic frequency in large populations.

The allelic frequency determination on mixtures of two different PCR products was carried out using the AGPase-based pyrosequencing system according to an embodiment of the present invention. FIG. 7 demonstrates proportional data obtained from different ratios of two mixed DNA samples, in which frequencies as low as about 5% could be detected accurately. The data illustrate that the AGPase-based pyrosequencing system according to an embodiment of the present invention can be used for rapid high throuput SNP allele frequency examination in genomic DNA pools.

Figure 8:
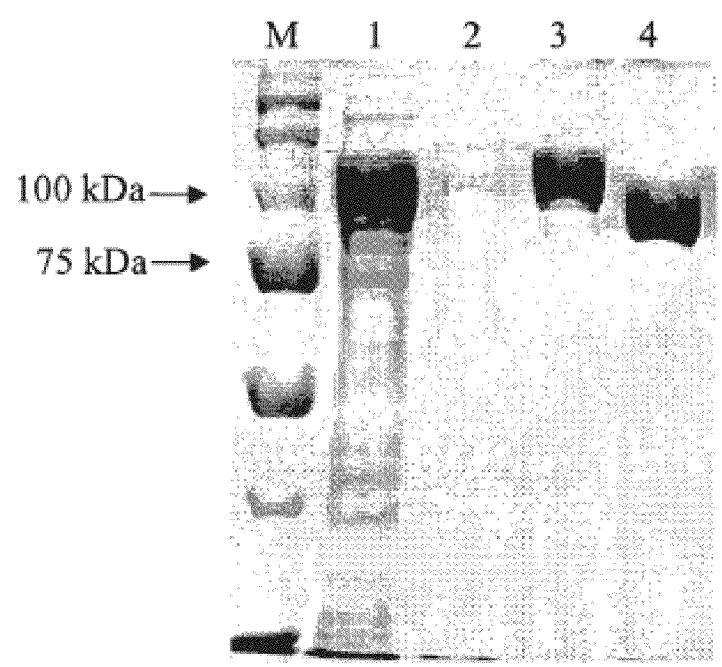
FIG. 8 shows purification of recombinant PPDK protein M, Low MW protein marker; 1, cell sonicate before purification; Protein fraction of 2, flow through of affinity chromatography; 3, eluent of affinity chromatography (TrxA-His-PPDK fusion protein); 4, eluent of gel filtration chromatography (cleaved PPDK)

A Comparison between the AGPase-based pyrosequencing system, the PPDK-based pyrosequencing system, and the conventional ATP sulfurylase-based pyrosequencing system In order to compare these three systems at the same conditions, all the components in the reaction mixtures were kept identical except for using APS and ATP sulfurylase in the conventional sequencing reaction, AMP, PEP and PPDK (cloned, expressed and purified with 15 U/mg protein activity, FIG. 8) in the PPDK-based reaction mixture, and ADPGlc and AGPase were used in the pyrosequencing mixture according to an embodiment of the present invention.

Figure 9A:
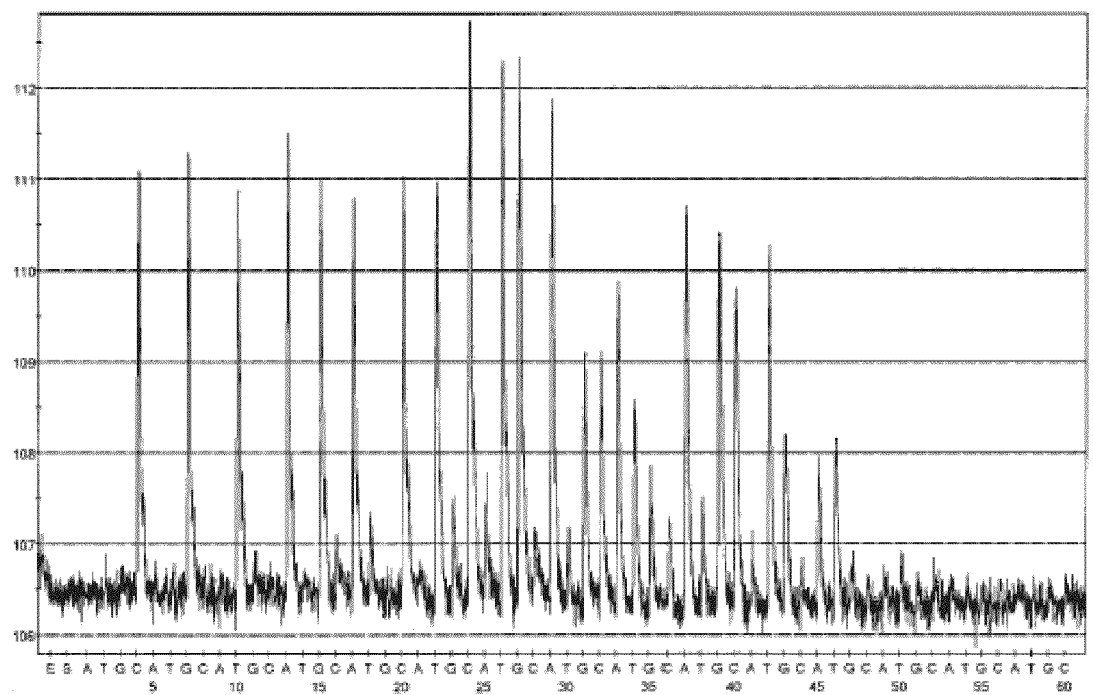
FIG. 9A, ATP sulfurylase-based system.
Figure 9B:
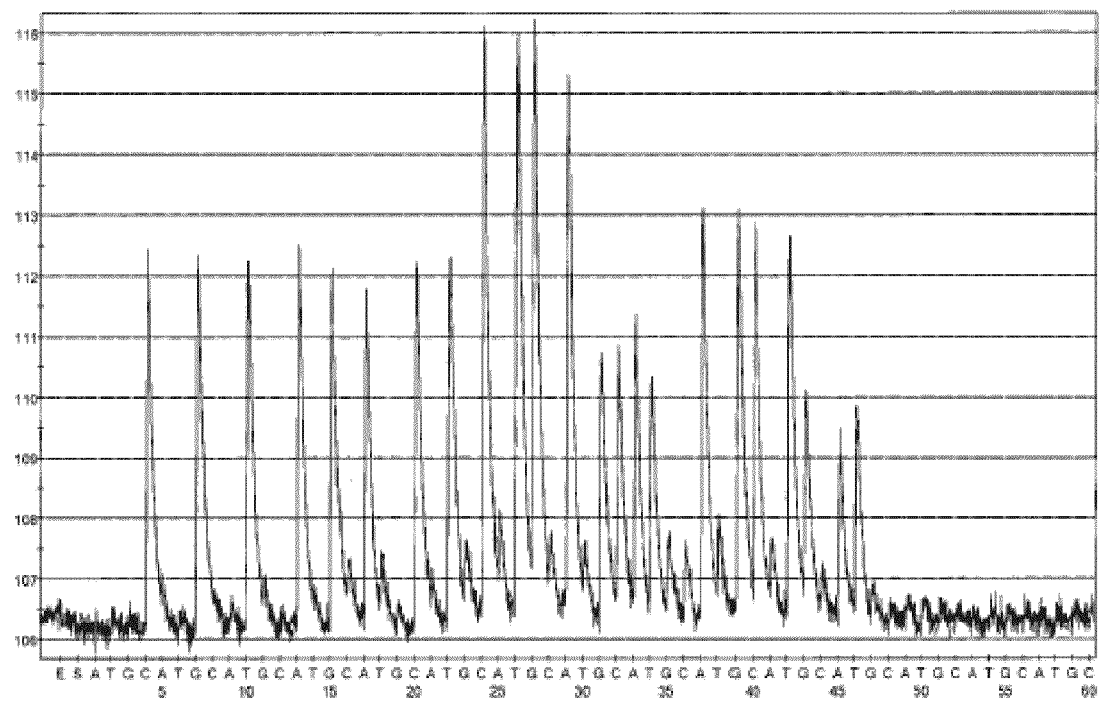
FIG. 9B, AGPase-based system.

Similar programs for SG_122 were obtained from the three sequencing systems when 0.5 µg of luciferase were used in the reaction mixtures (data not shown). To increase the detection sensitivity, a higher amount of luciferase is required as the height of the signal is determined by the activity of luciferase (FIG. 2D). However, a large amount of luciferase could not be used in the conventional system because of the high background signal generated from the side reaction between APS and luciferase (FIG. 4). The finding was further supported by the data shown in FIG. 9. When 0.75 µg of luciferase was applied in the AGPase or ATP sulfurylase-based pyrosequencing systems, similar signal intensities were obtained from 0.1 pmol of DNA template. Due to the high background in conventional ATP sulfurylase-based system, it was difficult to distinguish the signal generated from single nucleotide and double nucleotides (FIG. 9A). In contrast, sequencing signal from AGPase-based system according to an embodiment of the present invention clearly shows a linear relationship between the peak heights and the number of incorporated bases as is illustrated FIG. 9B.

Figure 9C:
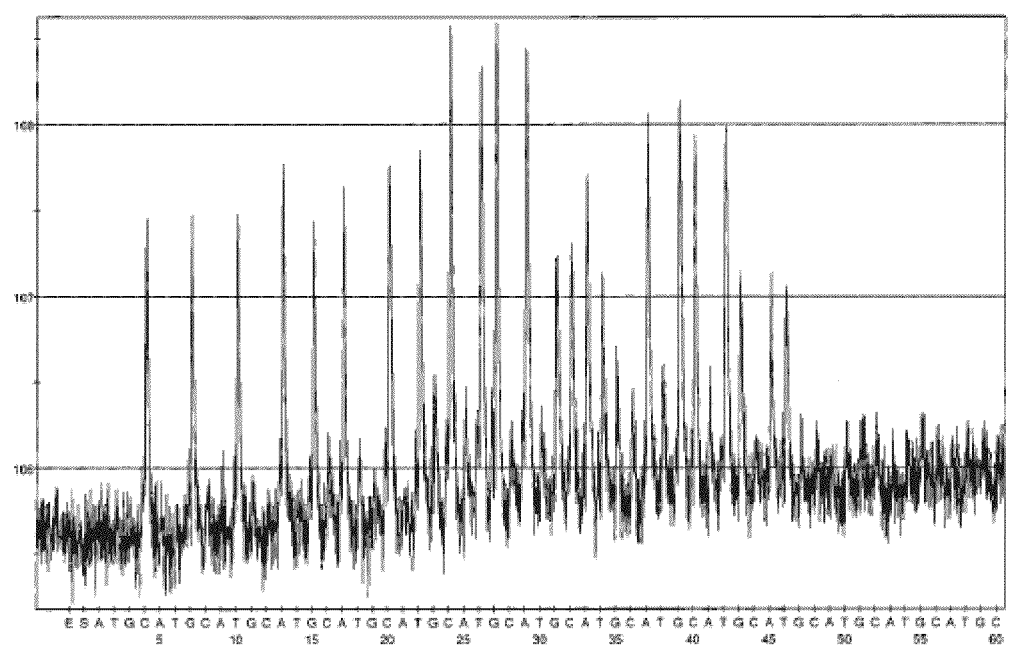
FIG. 9C, PPDK-based system.

As shown in FIG. 4, PPDK-based sequencing system showed low background during pyrosequencing. However, AMP and PEP are used as substrates in the reaction converting PPi to ATP where high concentration of AMP inhibits the luciferase-catalyzed reaction. In addition, PPDK shows the highest activity at 60° C. while pyrosequencing is carried out around room temperature. Hence, although a large amount of PPDK, e.g., 15 U/ml has been employed for pyrosequencing to compensate the low activity of PPDK at room temperature, the sequencing signal intensity is much lower as compared to the other two systems as is shown in FIG. 9C.

Figure 9D:
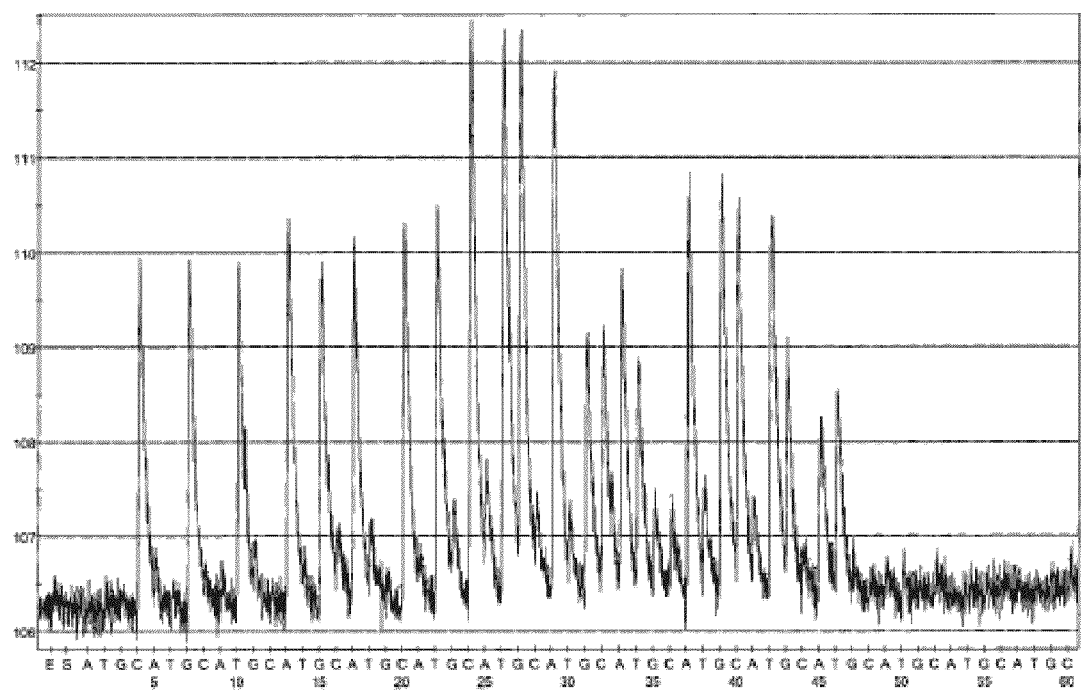

As is illustrated in FIG. 9D, according to an embodiment of the invention, sequencing on as low as about 0.025 pmol of DNA can be successfully carried out with negligible background when 1 µg of luciferase is employed in the AGPase-base system. The data demonstrate that the AGPase-based system according to an embodiment of the present invention allows the detection or sequencing of trace amount of DNAs by increasing the amount of luciferase.

The expression and purification of recombinant PPDK protein and the analysis on the background of AGPase/ADPGlc-, ATP Sulfurylase/APS- and PPDK/AMP-PEP-based pyrosequencing systems.

Luciferase Assay

The basic luciferase reaction mixture contains 60 mM tricine (pH 7.75), 0.5 mM EDTA, 5 mM magnesium acetate, 1 mM dithiothreitol, 100 µg D-luciferin, 0.1% bovine serum albumin, 0.4 mg/ml polyvinylpyr-rolidone (360,000), 0.5 µg of E. coli single-stranded DNA-binding protein and different amount of luciferase ranging from 300 µg to 1500 µg. The ATP sulfurylase-based assay system includes, besides of the basic reaction mixture, 5 µM APS and 15 mU ATP sulfurylase. Similarly, 0.08 mM PEP, 0.4 mM AMP and 0.6 U PPDK were added in PPDK -based system while 2.5 mM ADPGlc and 2.5 mU AGPase were added in AGPase-based system. The luminescence assays were performed using SpectraMax M5 MultiMode Microplate Reader (Molecular Devices, CA, USA). All the experiments were carried out in triplicates in three independent studies.

Cloning, Expression and Purification of PPDK

The ppdk gene from Microbispora rosea subsp. aerate was cloned into pETG-20A vector via Gateway cloing technology (Invitrogen, CA, USA). Recombinant PPDK was induced with 0.1 mM IPTG at 17° C. overnight and expressed with N-terminal TrxA and His-tags in T7 express competent *E. coli* cells (Stratagene, CA, USA). After sonication, the soluble rPPDK was extracted and purified on nickel resin according to the manufacturer's instructions (GE healthcare). 5-10% (v/v) of TEV protease was then added to the TrxA-His-PPDK protein fraction and incubated at 4° C. overnight to cleave the TrxA and His-tags from the fusion protein. Cleaved tags were removed by running the sample through Superdex 200 gel filtration column (GE healthcare, Uppsala, Sweden). The activity of purified recombinant PPDK was examined according to the method described by Eisaki, et al (Eisaki, N.; Tatsumi, H.; Murakami, S.; Horiuchi, T. *Biochim. Biophys. Acta*. 1999, 1431, 363-373 incorporated herein by reference).

Figure 3:
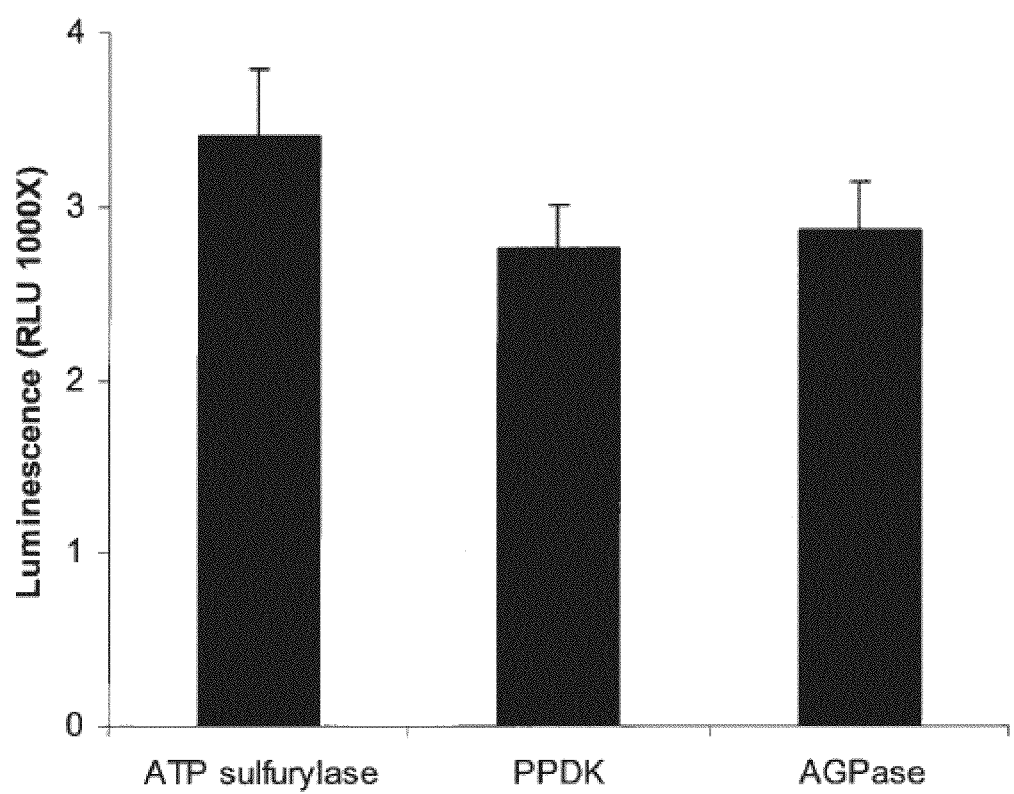
FIG. 3 shows the signal of 1 pmol of PPi from ATP sulfurylase/APS-, PPDK/AMP-PEP- and AGPase/ADPGlc-based luciferase assay.
Figure 4:
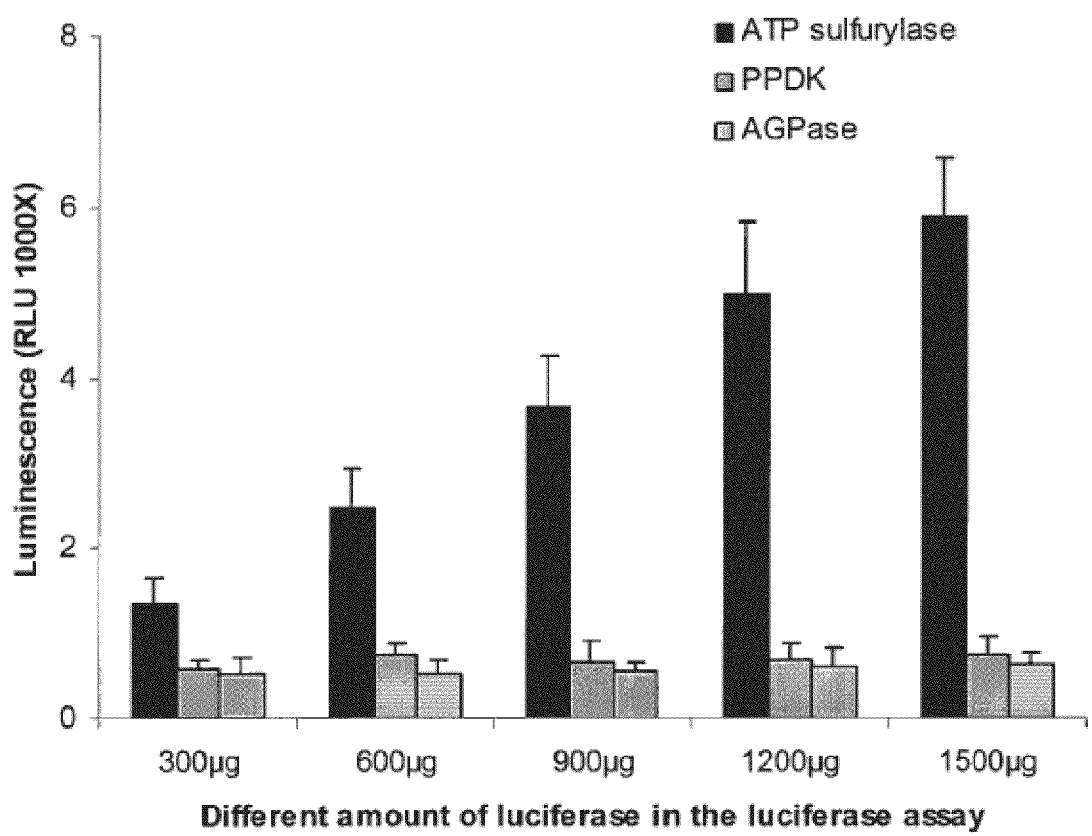
FIG. 4 shows the background of ATP sulfurylase/APS-, PPDK/AMP-PEP- and AGPase/ADPGlc-based methods in the luciferase assay.

The background generated by AGPase/ADPGlc-, ATP Sulfurylase/APS- and PPDK/AMP-PEP-based systems in the luciferase assay FIG. 3 illustrates the efficiency of three PPi utilizing enzymes, ATP sulfurylase, PPDK and AGPase, in converting 1 pmol of PPi to ATP in the luciferase reaction mixtures. The data demonstrates that these three enzymes produce comparable luminescence signals. However, as shown in FIG. 4, ATP sulfurylase produces a much higher background even in the presence of very low amount of luciferase (300 μg) as compared to PPDK and AGPase. In addition, the background generated in the ATP sulfurylase-based system increased with increasing amount of luciferase. In contrast, PPDK or AGPase-based system showed a relatively constant low background regardless of the amount of luciferase, which AGPase having a better performance than PPDK. The data reinforce the nonspecific reactivity of luciferase with APS leading to the high background in the conventional ATP sulfurylase-based system.

Expression and Purification of PPDK

As shown in FIG. 8, after induction, PPDK fusion protein was highly expressed and purified with molecular weight of about 111.4 KDa. To minimize the influence of tags on the activity of PPDK, TEV was used to cleave the TrxA and His-tags from the fusion PPDK protein. By the gel filtration chromatography purification, PPDK of about 96 kDa which was consistent with the predicted molecular weight was obtained with >about 95% purity. The purified PPDK showed 15 U/mg protein activity.

EXAMPLE 2

Chemiluminiscence Sensor for High-throughput DNA Sequencing

Materials and Methods

In various embodiments of the invention, the sequencing system 10 (e.g., a pyrosequencing system) can comprise various subsystems, for example, a fluidic subsystem for metering and control of various reagents entering the reaction platform (chamber) and transport of products away from the reaction platform (chamber), an imaging subsystem for acquisition of chemiluminesence intensity from the various reaction wells, a thermal subsystem providing temperature control for imaging the system and the reagents, or a combination thereof.

In this embodiment, the pyrosequencing reaction takes place in a reaction platform or chamber comprising an array of photolithoraphically fabricated 45 μm microwells with 45 μm depth on a fiberoptic face plate. Individual DNA beads are located in microwells, which are then packed with smaller sized enzyme beads and packing beads to ensure tight packing and prevent delamination and loss of beads during reagent flow.

In this embodiment, the nucleotides (AGCT) were flown sequentially. Each nucleotide flow cycle comprises the nucleotide flow followed by an apyrase flow to consume the unincorporated nucleotides, followed by substrate buffer flow to replenish the enzymes. The nucleotide flow cycle is repeated as many times as the number of base pairs desired to be sequenced.

In this embodiment, the entire process is automated and controlled by a visual interface developed in MATLAB. The image acquisition process is synchronized with the reagent flow process, and data is processed and stored automatically.

FIG. 1 shows the schematic diagram of the sequencing system 10 according to an embodiment of the invention. For example, the reagents can be held in an aluminum block holder designed to carry reagent tubes. The rear of this block can be in contact with a thermoelectric cooler to maintain the reagents at about 5° C. A multi-position valve and a peristaltic pump can facilitate reagent transport to and from the reaction platform or chamber. The core component of the sequencing system 10 in the embodiments is the reaction/imaging module. The fiberoptic face plate where the pyrosequencing reaction takes place in millions of picoliter sized wells is located in this module. The face plate is mounted flush on the camera face. On the other side of the face plate a silicon gasket cut to shape is sandwiched between the face plate and a plastic cover plate, which creates a tight seal for reagent flow. The entire reaction/imaging module is mounted on the thermoelectric cooling mechanism, which maintains the temperature below 0° C.

Results

Figure 10:
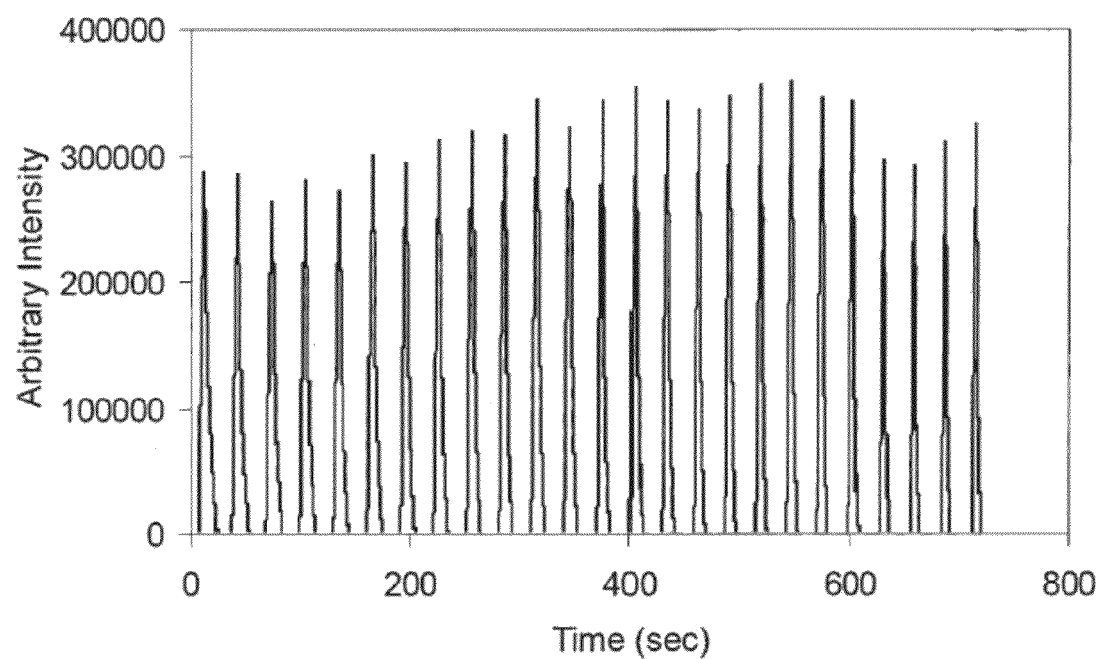
FIG. 10 demonstrates the modulation of chemiluminescence generated by directly flowing the pyrophosphate and deionized water sequentially for 30 seconds.

To quantify the bead loss due to long reads, nucleotide flow cycle was executed 25 times in the flow chamber. FIG. 10 shows the light intensity detected by a photomultiplier tube (PMT). The modulation of light intensity due to the flow of nucleotides followed by apyrase appears to be highly reproducible, with minimal loss of intensity over 25 cycles, which indicates negligible loss of enzyme coated beads during the 25 cycles. The solution collected from the output of the reaction chamber was processed through a coulter counter to enumerate the number of enzyme and DNA beads lost during the flow.

It was found that there was less than about 0.007% (6200 beads/μl beads are lost from $8.7 \times 10^6$ beads/μl) enzyme beads loss after 25 pyrophosphate dispensation cycles. The numbers are within experimental error and FIG. 10 demonstrates that the signal due to 25 cycles of pyrophosphate remains same providing that the enzyme bead lost is not a big concern.

Figure 11:
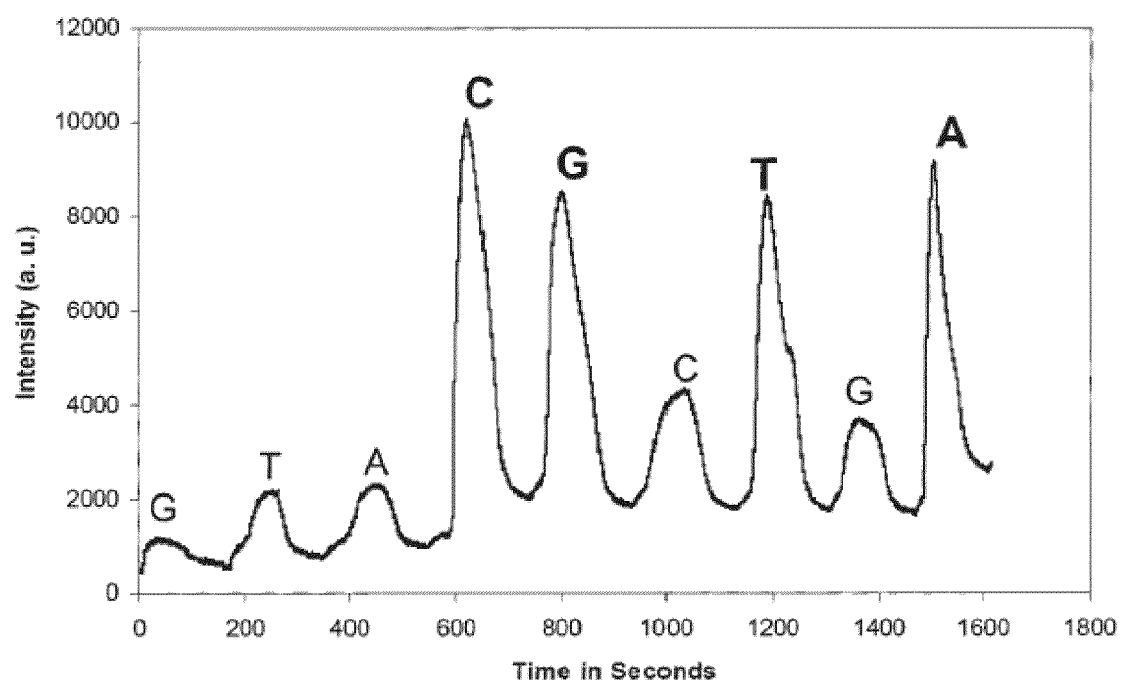
FIG. 11 shows sequencing of synthetic DNA string GOAT. The letters indicated in a regular font represent the flow of incorrect nucleotides, whereas the letters in a bold font represent the correct nucleotides.

FIG. 11 shows the sequencing of first four correct nucleotides (CGTA) of a custom-designed oligonucleotide (GCAT). The flow of incorrect nucleotides (non-bold font) generated trace amounts of light whereas the flow of correct nucleotides (bold font) produced higher signal levels. The insertion of wrong nucleotide flows in the correct sequence indicates the viability of this technique for de novo sequencing aside from providing information on the strength of the background signal for signal normalization.

Figure 12:
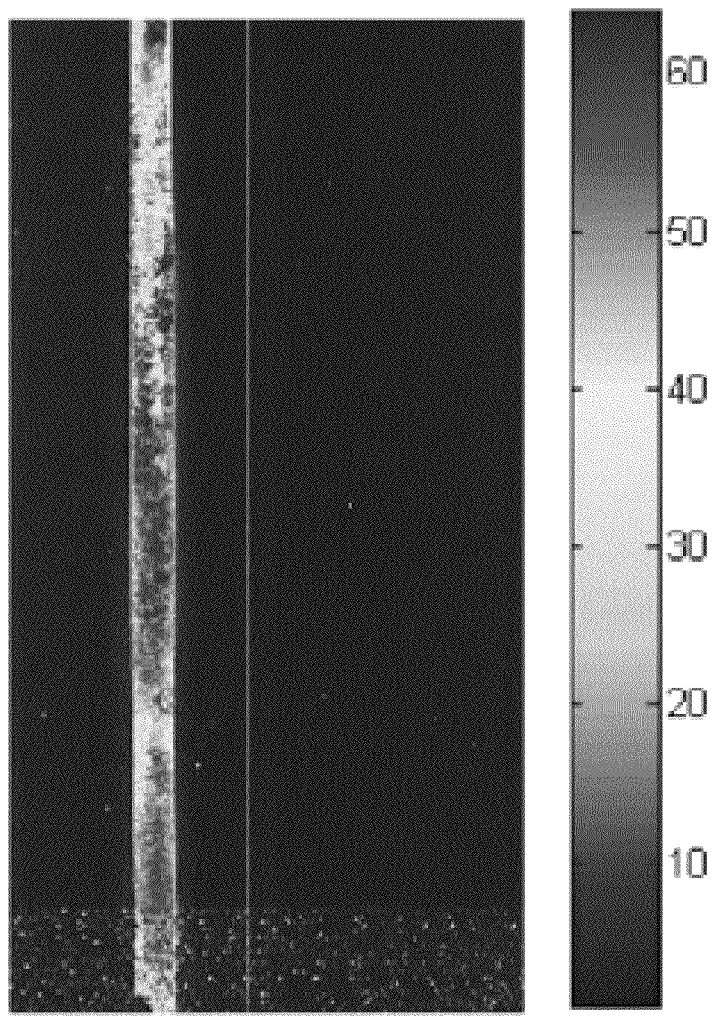
FIG. 12 is an image from the CMOS camera during sequencing. The strip indicates the rectangular area into which the DNA and enzyme-containing beads were deposited.
Figure 13:
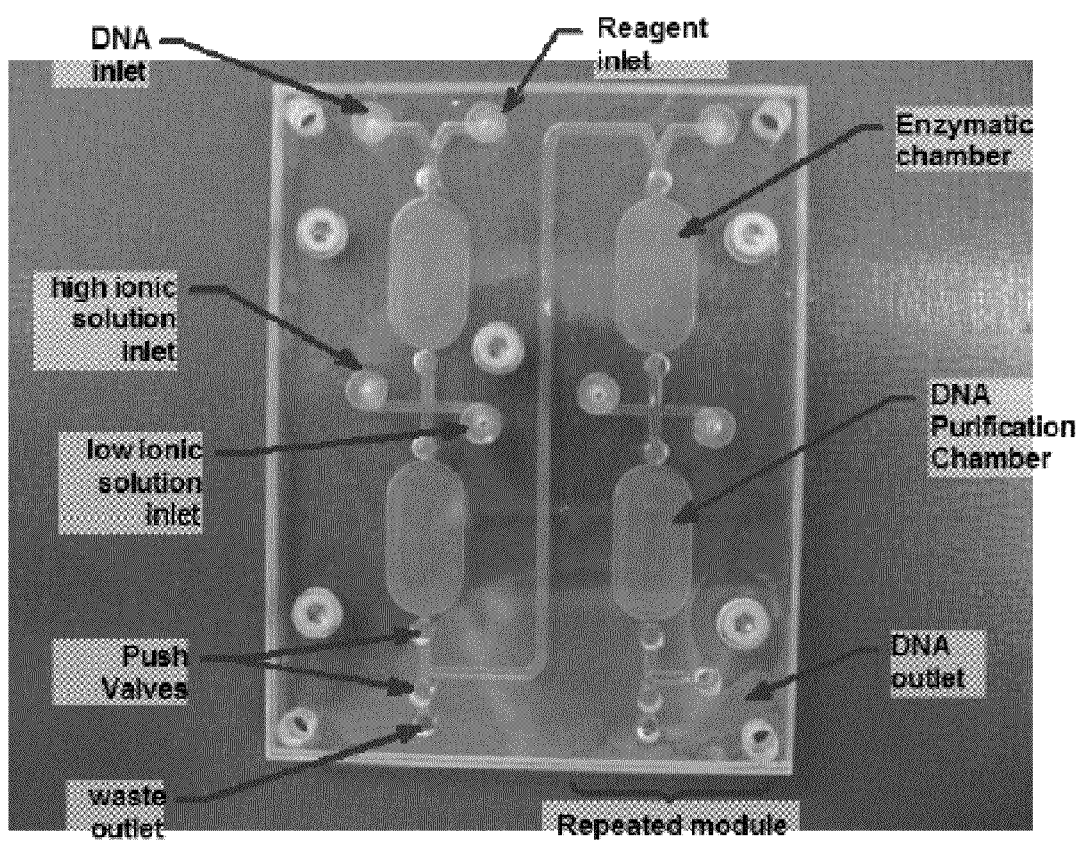
FIG. 13 illustrates a disposable module for an enzymatic and DNA purification process ($CO_2$ laser fabricated PMMA chip, size 90×70×9 $mm^3$)
Figure 14:
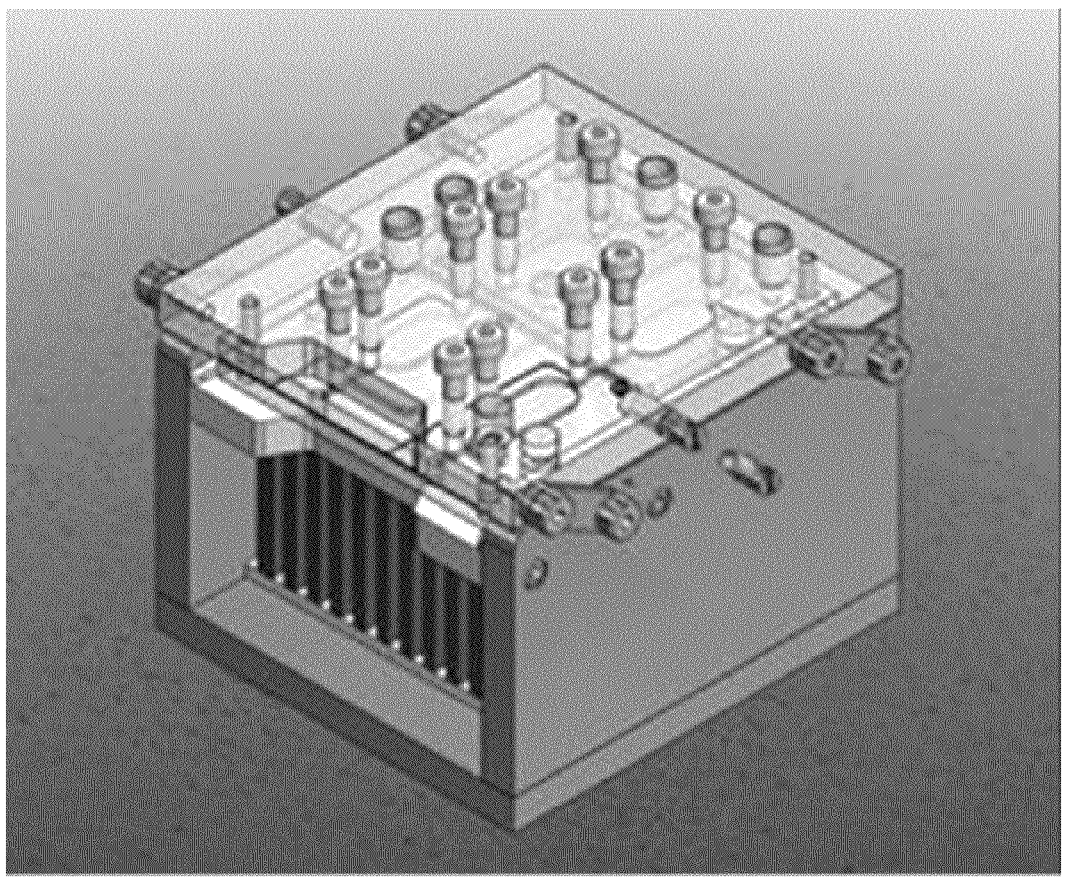
FIG. 14 illustrates an example of a permanent module with a heating (thermal) component.
Figure 15:
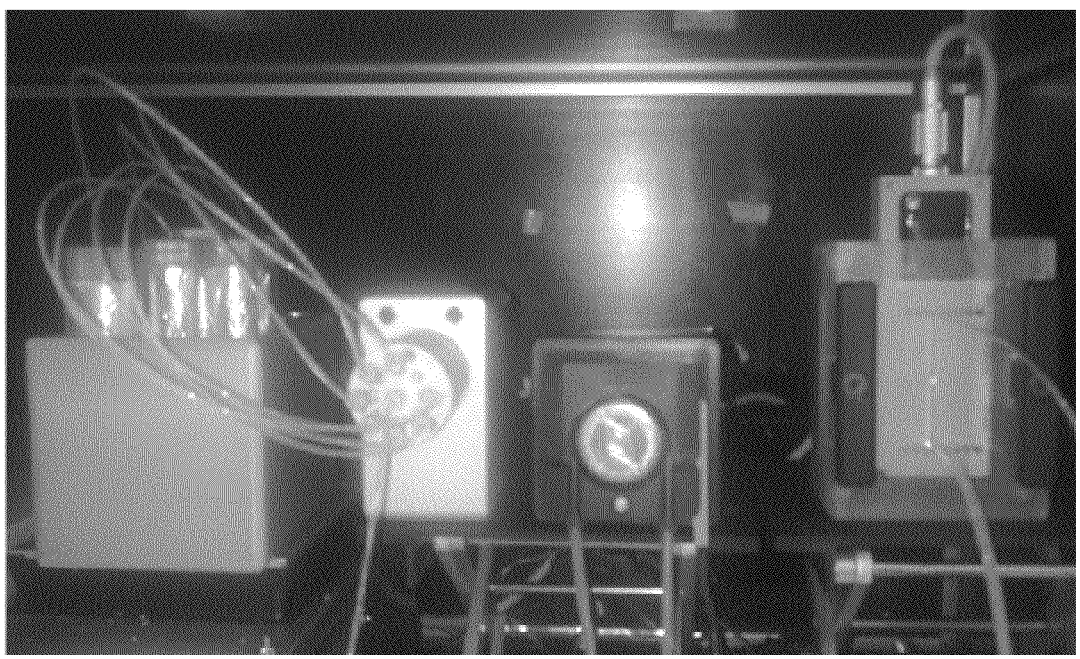
FIG. 15 illustrates an example of a pyrosequencer according to an embodiment of the invention.
Figure 16:
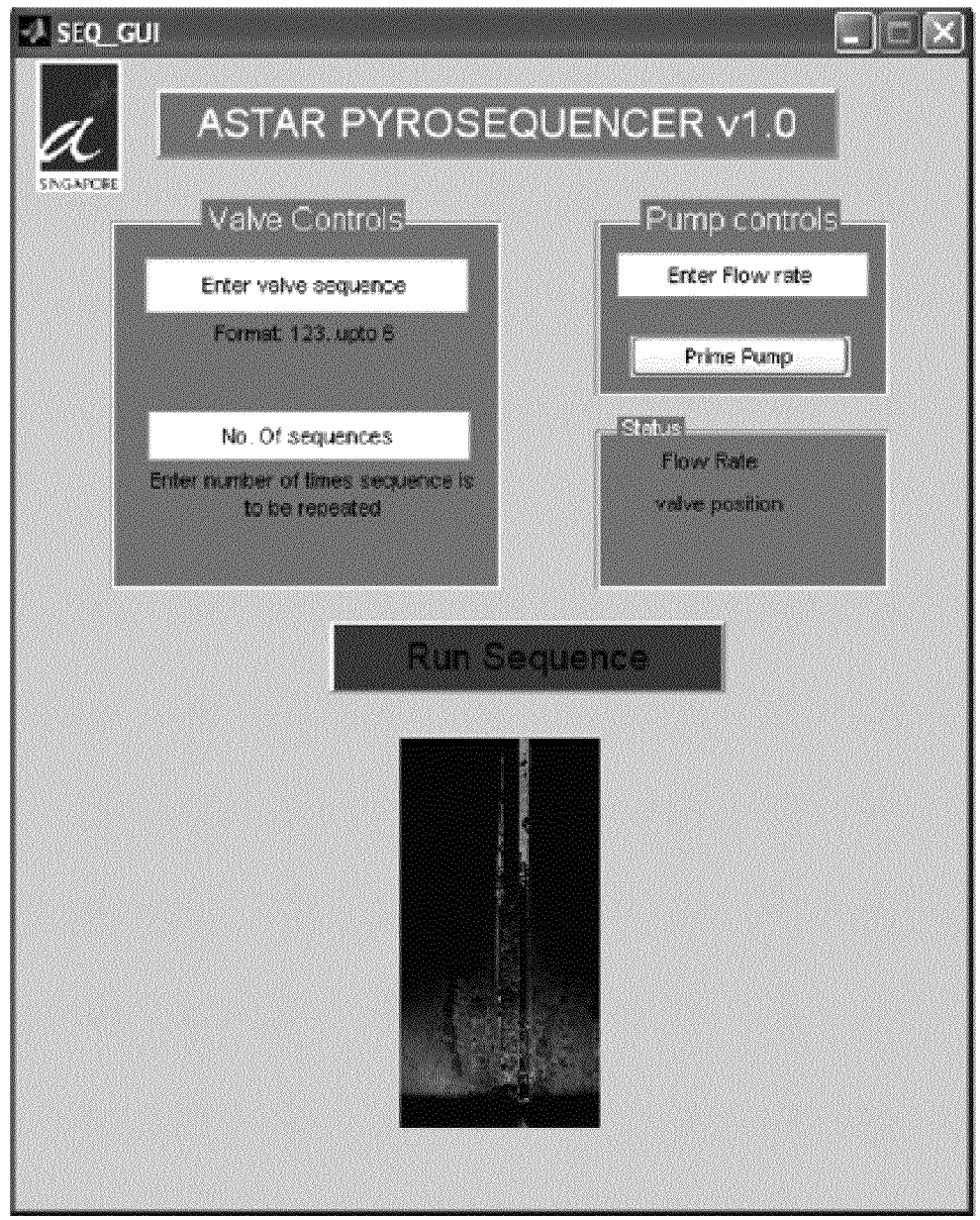
FIG. 16 is a graphical representation of a user interface for controlling all the units of the pyrosequencer, the sequencing order, and display of images in real time.
Figure 17:
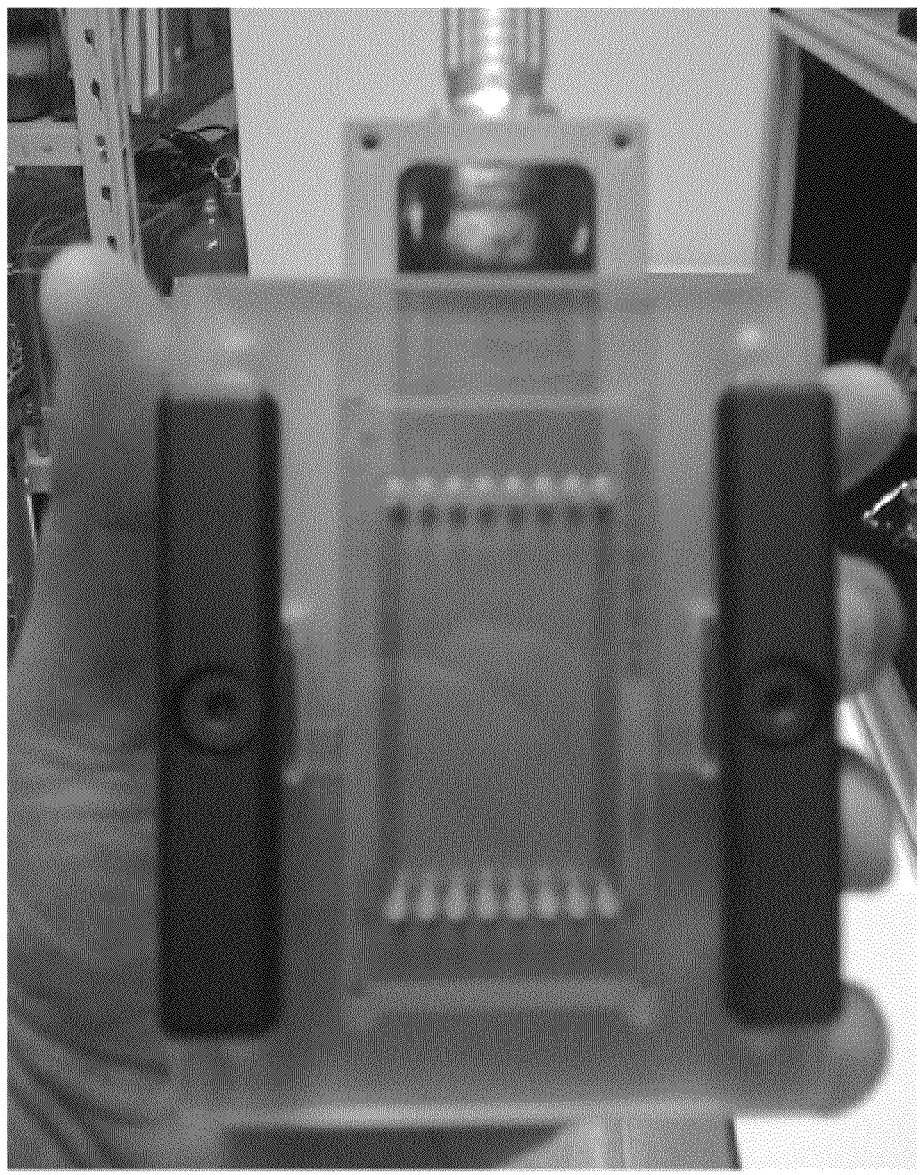
FIG. 17 illustrates a handheld chip holder with the CMOS sensor.

In another embodiment, the chemiluminescence generated was captured using well-to-pitch matched CMOS image sensor (FIG. 12). A rectangular section of the face plate in contact with the image sensor was populated with the enzyme beads. A flow channel was fashioned with silicone sheet to serve as a flow chamber on the face plate. Upon flowing the correct nucleotide, the light generated by the enzymatic reaction cascade was captured by the image sensor. This indicates that the signal strength generated by the reaction is sufficiently high for CMOS based detection.

Examples of various other embodiments are further shown in FIGS. 13 to 17.

Thus the various embodiments described above in connection with the sequencing system indicate that this system is viable for use in pyrosequencing. The system is able to distinguish between the correct and incorrect nucleotide flow, thereby demonstrating the potential for de novo sequencing. Multiple cycle (25) nucleotide flows described above demonstrated that the loss of enzyme and DNA beads from the reaction chamber was minimal. In various embodiments, with the use of higher resolution camera in combination with fiber optic face plate with reduced fiber diameter can circumvent the need for registration and greatly improve resolution of the system. Due to the potential for achieving higher read-length (for example, up to about 500), inexpensive reagents and sensors, this approach is time and cost efficient in comparison to other conventional sequencing platforms.

Although specific embodiments of the invention have been described and illustrated, such embodiments should not to be construed in a limiting sense. Various modifications of form, arrangement of components, steps, details and order of operations of the embodiments illustrated, as well as other embodiments of the invention, will be apparent to persons skilled in the art upon reference to this description. It is therefore contemplated that the appended claims will cover such modifications and embodiments as fall within the true scope of the invention. In the specification including the claims, numeric ranges are inclusive of the numbers defining the range. Citation of references herein shall not be construed as an admission that such references are prior art to the present invention.

The invention claimed is:

1. A method for sequencing a target nucleic acid molecule, the method comprising:
   (a) contacting the target nucleic acid molecule with a pyrophosphate sequencing reagent, the pyrophosphate sequencing reagent comprising:
      (i) a nucleotide triphosphate,
      (ii) a polymerase,
      (iii) a pyrophosphate to ATP converting enzyme comprising adenosine diphosphate (ADP)-glucose pyrophosphorylase and a substrate ADP-glucose; and
      (iv) an ATP detecting enzyme; and
   (b) detecting a resulting optical signal wherein the optical signal is indicative of a reaction of the pyrophosphate sequencing reagent with the target nucleic acid molecule, thereby sequencing the nucleic acid molecule.

2. The method of claim 1 wherein the pyrophosphate sequencing reagent further comprises a nucleotide degrading enzyme.

3. The method of claim 2 wherein the nucleotide degrading enzyme is apyrase.

4. The method of claim 1 wherein the target nucleic acid molecule comprises an amount of DNA of 0.025 pmol or less.

5. The method of claim 1 wherein the target nucleic acid molecule is immobilized on a solid support.

6. The method of claim 1 wherein the ATP detecting enzyme is luciferase.

7. The method of claim 1 wherein the contacting and detecting steps are performed in an apparatus comprising:
   (a) a reaction platform comprising a plurality of wells, each of the plurality of wells entrapping a sample solid support having an immobilized sample nucleic acid molecule;
   (b) a reagent source in fluid communication with each of the plurality of wells for flowing a reagent to each of the plurality of wells and for transporting a product away from each of the plurality of wells while the sample solid support remains entrapped in the respective well; and
   (c) an imaging sensor mounted on the reaction platform for acquisition of chemiluminescence intensity from each of the plurality of wells.

8. The method of claim 6 wherein the luciferase is present in an amount ranging from 0.3μg to 3 μg.

9. The method of claim 1 wherein a homopolymeric region of the target nucleic acid molecule is sequenced.

10. The method of claim 1 wherein the target nucleic acid molecule comprises an amount of DNA of 0.025 pmol or less, wherein the ATP detecting enzyme is luciferase, and wherein the luciferase is present in an amount of 1.5 μg to 3 μg.

* * * * *